(12) United States Patent
Mechali et al.

(10) Patent No.: US 8,753,887 B2
(45) Date of Patent: Jun. 17, 2014

(54) USE OF A CELLULAR EXTRACT FOR A MITOTIC REMODELING OF CHROMOSOMES

(75) Inventors: Marcel Mechali, Montferrier sur Lez (FR); Jean-Marc Lemaitre, Asperes (FR)

(73) Assignee: Centre National de la Recherche Scientifique, Paris (FR)

( * ) Notice: Subject to any disclaimer, the term of this patent is extended or adjusted under 35 U.S.C. 154(b) by 1238 days.

(21) Appl. No.: 12/088,697

(22) PCT Filed: Sep. 29, 2006

(86) PCT No.: PCT/EP2006/009499
§ 371 (c)(1),
(2), (4) Date: Sep. 8, 2008

(87) PCT Pub. No.: WO2007/039258
PCT Pub. Date: Apr. 12, 2007

(65) Prior Publication Data
US 2010/0184225 A1    Jul. 22, 2010

Related U.S. Application Data

(60) Provisional application No. 60/721,978, filed on Sep. 30, 2005.

(51) Int. Cl.
| C12N 15/00 | (2006.01) |
| C12N 5/071 | (2010.01) |
| C12N 5/07 | (2010.01) |
| C12N 5/10 | (2006.01) |
| C12N 5/02 | (2006.01) |
| C12N 5/16 | (2006.01) |
| C12N 5/076 | (2010.01) |
| C12N 5/075 | (2010.01) |
| A01K 67/027 | (2006.01) |

(52) U.S. Cl.
CPC ...... *C12N 5/16* (2013.01); *C12N 5/061* (2013.01); *C12N 5/0609* (2013.01); *C12N 5/0696* (2013.01); *C12N 2500/80* (2013.01); *A01K 67/0271* (2013.01)
USPC ............ 435/455; 435/366; 435/354; 435/377

(58) Field of Classification Search
CPC ......................... C12N 2500/18; A01K 67/0271
USPC ........................................................ 435/455
See application file for complete search history.

(56) References Cited

U.S. PATENT DOCUMENTS 6,753,457 B2 *   6/2004   Wangh ............................ 800/24

OTHER PUBLICATIONS

Dmitrov and Wolffe, EMBO J, 1996, 15:5897-5906.*
Campbell Biology of Reproduction, 50:1385-1393, 1994.*
Campbell, Cloning, 1:3-15, 1999.*
Liu, Mol Reprod Dev., 47:255-264, 1997.*
Wangh, Journal of Cell Science, 108:2187-2196.*
Thomson et al. PNAS, 92:7844-7848 Aug. 1995.*
NIH (Stem Cells: Scientific Progress and Future Research Directions, Department of Health and Human Services, Chapter 1, pp. 1-3, Jun. 2001.*
Osonoi, Human Cell, 2011, 24:30-34.*
Djuric and Ellis, 202, Stem Cell Research and Therapy, 2010,1:3.*

* cited by examiner

*Primary Examiner* — Valarie Bertoglio
(74) *Attorney, Agent, or Firm* — Young & Thompson

(57) ABSTRACT

The present invention relates to the use of a female germinal cell (egg) extract of pluricellular organisms in M-phase of the cell cycle for a mitotic remodeling of chromosomes of donor cells of pluricellular organisms, wherein the mitotic remodeling confers to the nucleus of the donor cells the ability to adapt themselves to the early embryonic development, in particular to the replication phases, in order to carry out the embryonic development or to obtain stem cells.

3 Claims, 14 Drawing Sheets

Figure 1A:
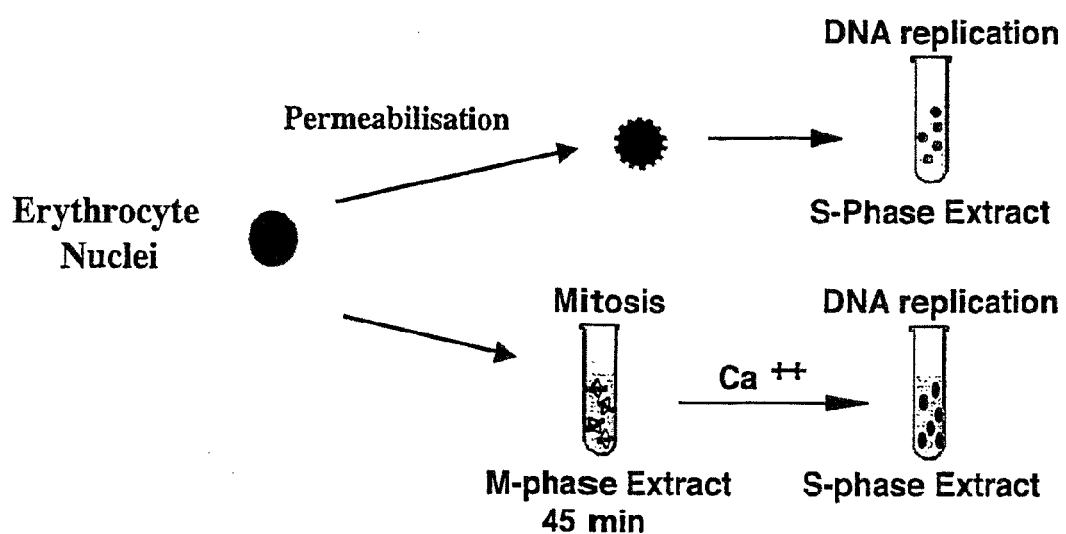

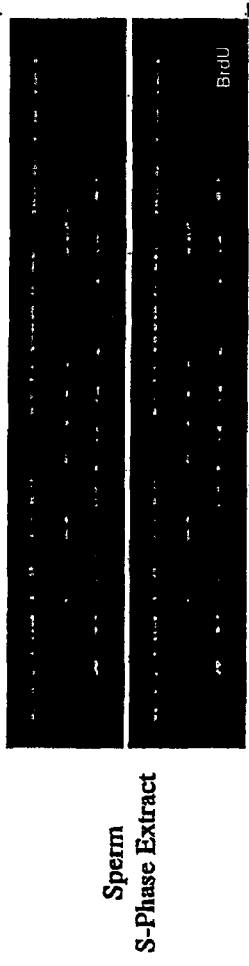
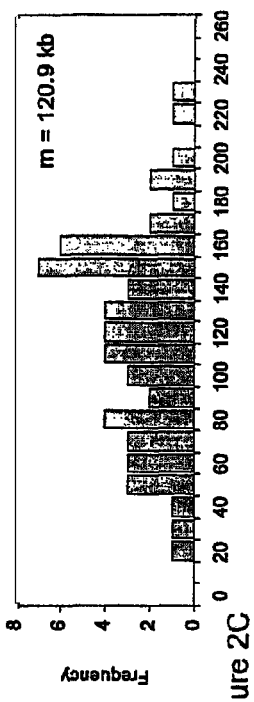
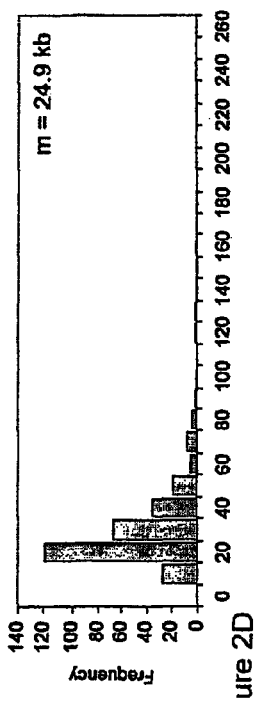
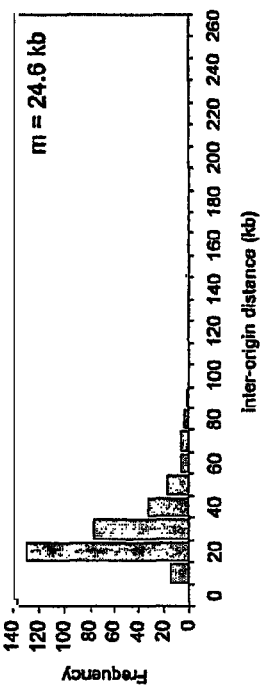
Figure 2A
Figure 2B
Figure 2C
Figure 2D

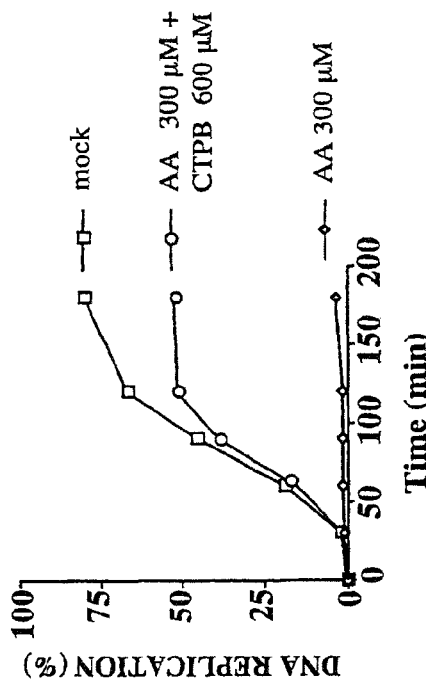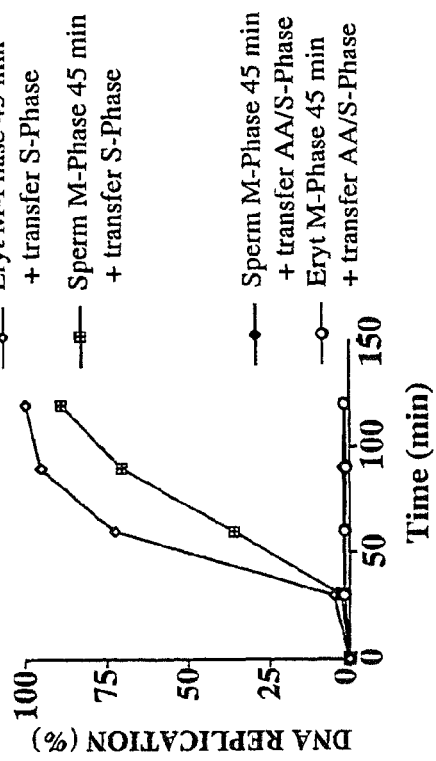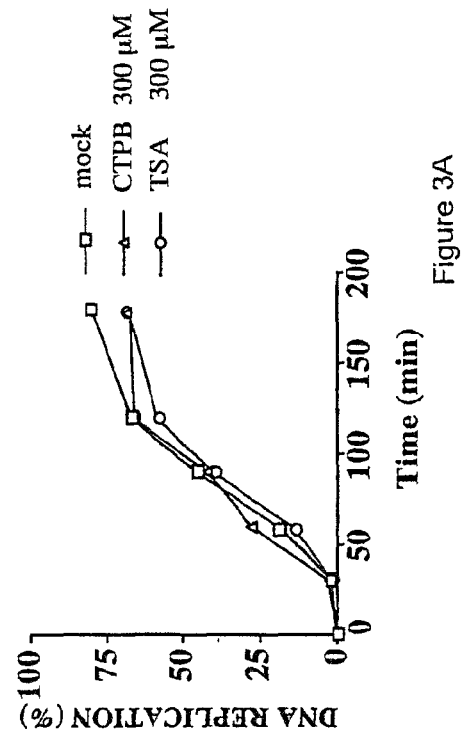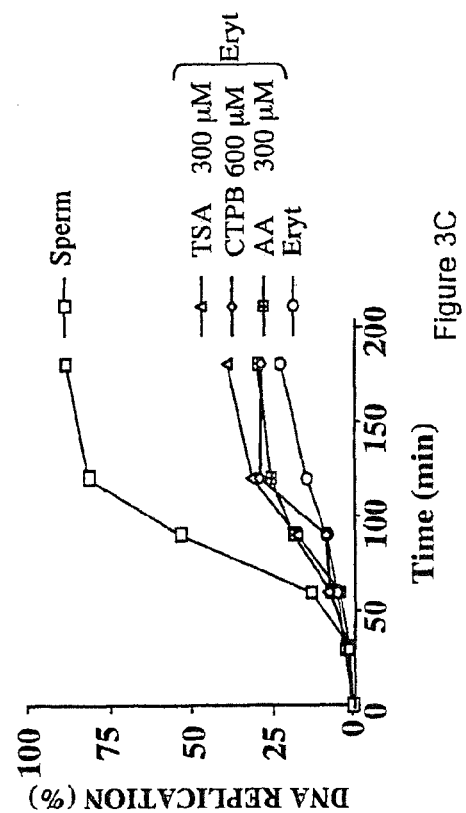
Figure 3A
Figure 3B
Figure 3C
Figure 3D

DNA Loop size = H x 2 x 2.3 (kbp)

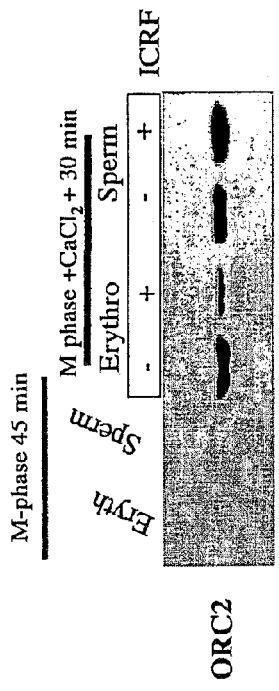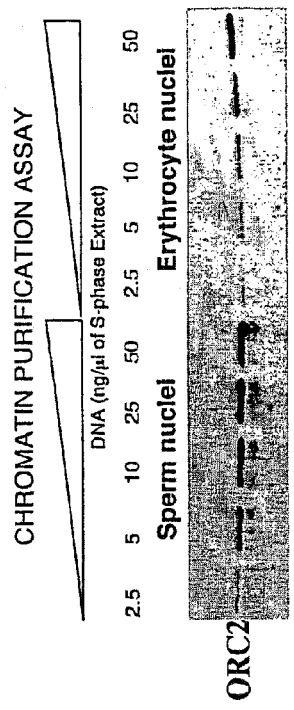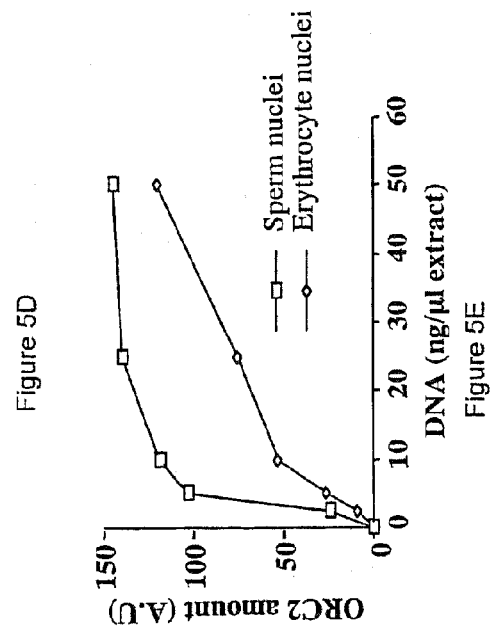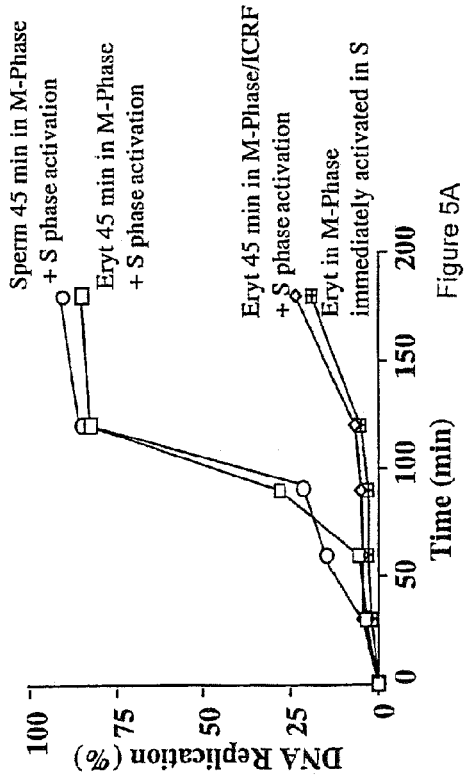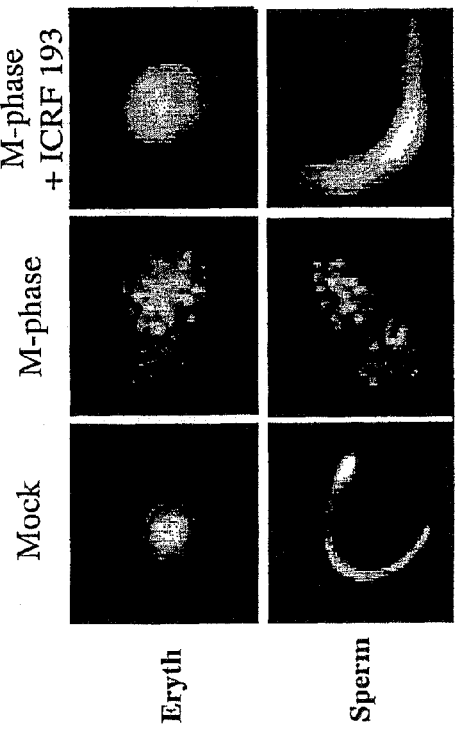

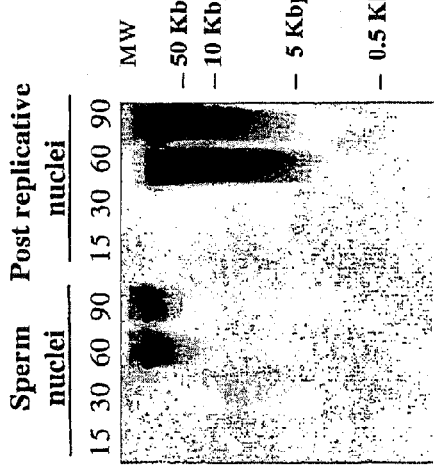
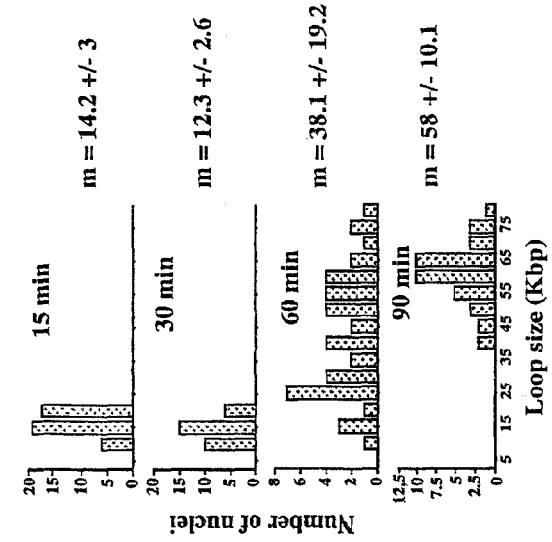
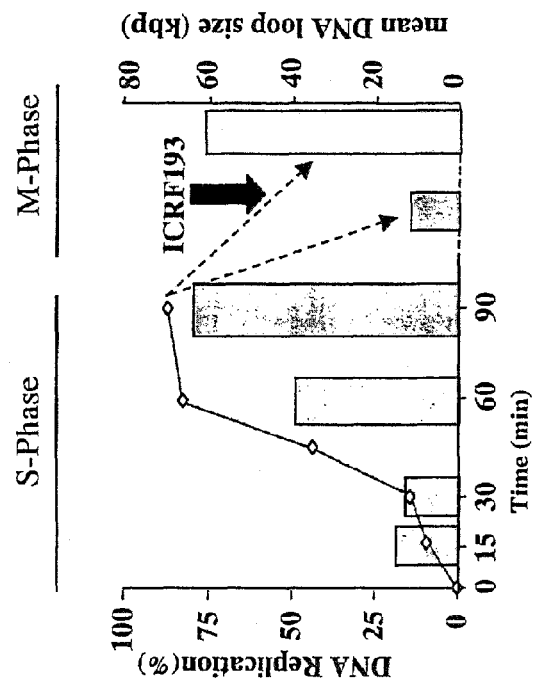

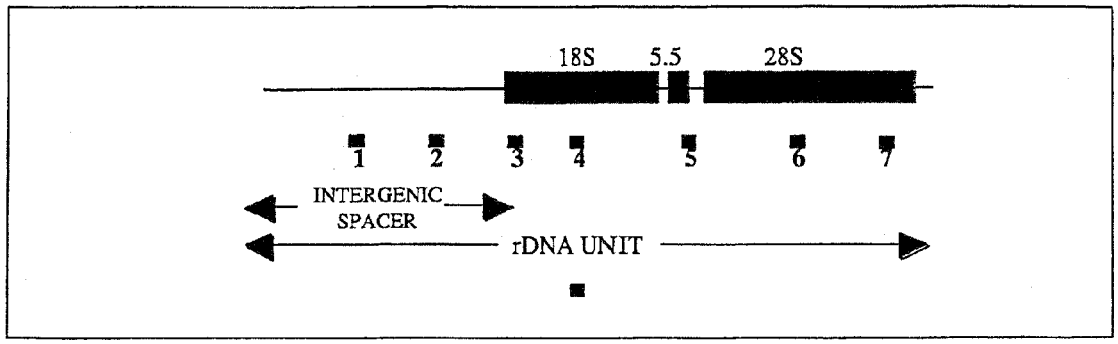
Figure 10A
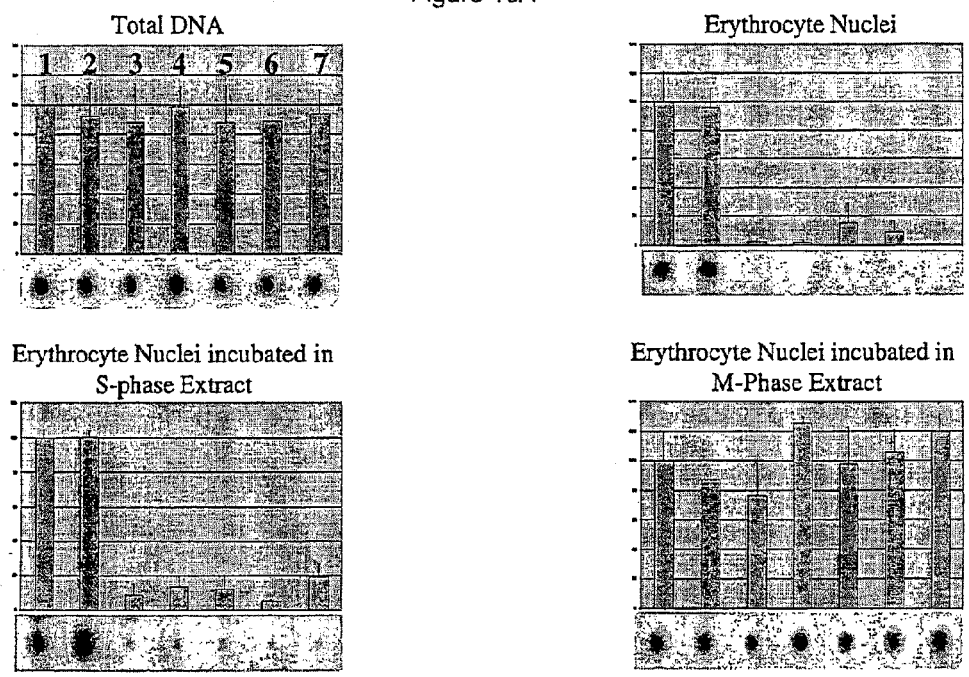
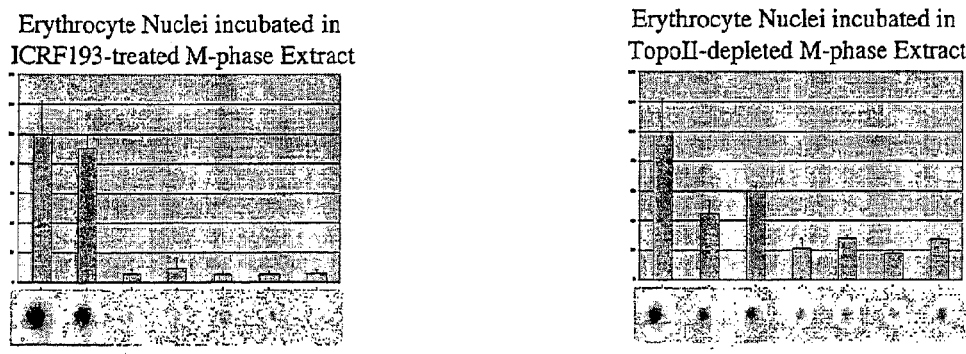
Figure 10B

CHROMATIN PURIFICATION ASSAY

USE OF A CELLULAR EXTRACT FOR A MITOTIC REMODELING OF CHROMOSOMES

Nuclear transfer is a powerful method that can be used to produce cloned animals and to obtain new sources of multi-potential cells from differentiated tissues. By transplanting nuclei from differentiated amphibian or mammalian cells into enucleated eggs, blastula or blastocyst embryos can be obtained which can develop into entire animals or used to form a wide range of tissues and cell types (Gurdon et al., 2003). The potential ability to deliver supplies of multipotential cells, which hold great promise for cell-based therapies for numerous disorders, makes nuclear transfer an appealing alternative to the difficult practice of directly isolating natural stem cells from normal adult tissues (McKay, 2000).

Despite its many advantages, however, nuclear transplantation is often inefficient due to the difficulty involved in completely reprogramming differentiated adult nuclei for the events of early development. Indeed, it is known that the ability of the egg to reset the epigenetic marks of adult donor cells is determinant for the efficiency of nuclear cloning. Identifying the specific epigenetic properties of differentiated cell nuclei that must be reset before development can begin anew, and how such resetting can be efficiently achieved, thus represents a challenge of major biological and medical significance.

Various methods have been identified that can enhance the efficiency of nuclear transplantation. In amphibians, for example, cloning efficiency, is substantially improved by serial nuclear transfers. This consists of transferring a nucleus from a differentiated donor cell to an enucleated egg, allowing the cell to undergo several divisions, and then using the daughter nuclei as donors for a second nuclear transfer experiment (Gurdon, 1962). Injections of nuclei into maturing oocytes instead of eggs (DiBerardino and Hoffner, 1983) led to the hypothesis that components of maturing oocytes may enable the injected nucleus to respond to DNA synthesis-inducing factors in activated eggs (Leonard et al., 1982).

One possible factor contributing to the low efficiency of cloning experiments is that the chromosome organization of differentiated adult nuclei may not be well adapted for DNA replication. DNA replication occurs at several hundred foci within the nuclei of proliferating cells, with origins that appear to be synchronously set up prior to entry into S phase (Jackson, 1990) These foci are stable throughout S phase, and can persist across successive divisions (see (Berezney et al., 2000) for review).

Animal cloning represents a major challenge in various fields, from the conservation of animal species, the production of proteins, such as therapeutic proteins, by cloned animals, to the therapeutic cloning, particularly for obtaining stems cells useful for autologous transplants.

However, the efficiency of the current cloning techniques needs to be improved to in order to contemplate large scale applications.

The present invention relates to the use of a cell extract for a mitotic remodeling of chromosomes and nuclei in order to adapt them to the cell division characteristics of the early development and make them more suitable for embryogenesis.

Another aspect of the invention is to provide a composition comprising nuclei of donor cells or donor cells and a cell extract.

Another aim of the present invention is to provide a process for cloning cells of non-human pluricellular organisms.

Another aim of the invention is also to provide a process for obtaining multipotent or totipotent stem cells of pluricellular organisms.

The present invention relates to the use of a female germinal cell (egg) extract of pluricellular organisms in M-phase of the cell cycle for a mitotic remodeling of chromosomes of donor cells of pluricellular organisms, wherein the mitotic remodeling confers to the nucleus of the aforesaid donor cells the ability to adapt themselves to the early embryonic development, in particular to the replication phases, in order to carry out the embryonic development or to obtain stem cells.

The expression "germinal cell" refers to a cell susceptible to form the gametes.

The expression "female germinal cell", also called "egg" relates a cell at any stage of the oogenesis, particularly primordial germ cells, oogonia and oocytes.

The germinal cell extract is preferentially made from eggs which are arrested at the metaphase stage of the second meiotic division.

The "female germinal cell (egg) extract" is a cell extract obtained by the implementation of the process as described in Menut et al., 2001 (referred as CSF extract).

In what precedes and what follows, the female germinal cell extract can be replaced by a mitotic non-human early embryo of vertebrates. Said mitotic non-human early embryo of vertebrates may be obtained by the process described in Lemaitre et al. 1998.

The expression "pluricellular organism" (or "multicellular organism") refers to living organisms that are composed of several cells. In said multicellular or pluricellular organisms, the similar cells usually aggregate in tissues and the specific arrangements of different tissues form organs.

The cell cycle is the cycle of life of a cell which undergoes division. The cell cycle comprises:
the M-phase, which corresponds to the mitosis wherein the nucleus is divided, and
the interphase, which is constituted by the three following phases:
  G1-phase, which corresponds to the period of the interphase that precedes the DNA synthesis,
  S-phase, which corresponds to the phase of DNA synthesis,
  G2-phase, which corresponds to the period of the interphase that follows the DNA synthesis.

The "replication phase" corresponds to the phase of DNA synthesis, i.e. the S-phase of the cell cycle.

The expression "mitotic remodeling" refers to major changes in the organization of the chromosomes or chromatin or the nucleus, which occur at mitosis.

By using the term "chromosome", it is referred to the association of DNA and proteins that is present in the nucleus of all eukaryote cells, and which is particularly apparent during mitosis and meiosis.

The expression "early embryonic development" refers to the period from fertilized ovum up to the occurrence of the first differentiated cells (not included).

In *Xenopus*, the early embryonic development corresponds to the period from the fertilized egg up to a period encompassing the mid-blastula transition and gastrulation and first transcriptions in the embryo.

The expression "adapt themselves to the early embryonic development" means that they can function as early embryonic nuclei.

One aim of the invention is to use the aforesaid female germinal cell (egg) extract for a mitotic remodeling of chromosomes of donor cells in order to carry out the embryonic development. The expression "carry out the embryonic development" means that the nucleus of the donor cell can be introduced in an enucleated egg in order to perform its embryonic development.

Another aim of the invention is to use the aforesaid female germinal cell (egg) extract for a mitotic remodeling of chromosomes of donor cells in order to obtain stem cells.

Stem cells are primal undifferentiated cells that retain the ability to divide and can differentiate into other cell types. Totipotent stem cells can differentiate into embryonic and extra-embryonic cell types. Pluripotent stem cells originate from totipotent cells and can give rise to progeny that are derivatives of the three embryonic germ layers, mesoderm, ectoderm and endoderm.

The invention particularly relates to the use as defined above, wherein the donor cells are differentiated somatic cells.

Somatic cells are any cells other than oocytes and spermatozoids.

"Differentiated somatic cells" are somatic cells that are specialized in a particular function and that do not maintain the ability to generate other kinds of cells or to revert back to a less differentiated state.

The differentiated somatic cells may particularly originate from any kind of tissue of the organism, such as skin, intestine, liver, blood, muscle, etc.

The invention also relates to the above mentioned use, wherein the female germinal cell (egg) extract of pluricellular organisms is in M-phase of the cell cycle and contains the material necessary to carry out the division cycles and the material necessary to allow the mitotic remodeling of the chromosomes.

In a preferred embodiment, the invention relates to the use as defined above, wherein the pluricellular organisms are vertebrates chosen among mammals, in particular humans, birds, reptiles and amphibians, and particularly *Xenopus*.

In the context of the present invention, the mitotic extract and the donor cell may originate from different species. In a preferred embodiment of the invention, the mitotic extract and the donor cell originate from the same species.

The invention relates to a composition comprising nuclei of cells of pluricellular organisms, preferentially permeabilized, and an extract of a female germinal cell (egg) extract of pluricellular organisms in M-phase of the cell cycle.

To improve the entrance of the female germinal cell extract into the nuclei, the nuclear envelope can be permeabilized. The permeabilization of the nuclei is achieved by the techniques well known in the art, such as the use of a chemical agent, or a mild detergent, or an enzyme that can make small holes in the nuclear envelope, as lysolecithin, or via a mechanical process which can at least partly open the nuclear envelope, for example pipetting.

The invention also relates to a composition comprising cells of pluricellular organisms, possibly permeabilized, and a female germinal cell (egg) extract of pluricellular organisms in M-phase of the cell cycle.

To improve the entrance of the female germinal cell extract into the cells, the cell membrane can be permeabilized. The permeabilization of the cell membrane is achieved by the techniques well known in the art, such as the use of a chemical agent or a mild detergent, such as digitonine, Triton, or an enzyme that can make small holes in the cell membrane, as lysolecithin, or via a mechanical process which can at least partly open the cell membrane, for example pipetting.

The present invention particularly relates to a composition as defined above, wherein the cells of pluricellular organisms are differentiated somatic cells.

In a preferred embodiment of the invention, the invention relates to a composition as defined above, wherein pluricellular organisms are vertebrates chosen among mammals, in particular humans, birds, reptiles and amphibians, and particularly *Xenopus*.

In another embodiment, the present invention relates to nuclei of cells of pluricellular organisms, possibly permeabilized, containing a female germinal cell (egg) extract of pluricellular organisms in M-phase of the cell cycle.

According to the present invention, the nuclei can be used in a cell context or in an in vitro context, that is to say after extraction for the cells. The nuclei can be extracted from the cells by the techniques well known in the art, such as cell breakage by incubation in a hypotonic buffer, use of a dounce homogeneizer or a potter homogeneizer or an isotonic buffer containing sucrose, glycerol or similar stabilizing agent and use of a potter homogeneizer or dounce homogeneizer able to open or disrupt the cell membrane.

The nuclei are stored in specific conditions to maintain their integrity, such as storage at $-20°$ C., $-80°$ C. or in liquid nitrogen in conditions known to be used to store oocytes or early embryos.

The present invention particularly relates to nuclei of cells of pluricellular organisms, possibly permeabilized, which were reprogrammed by a female germinal cell (egg) extract of pluricellular organisms in M-phase of the cell cycle.

The term "reprogrammed" means that the nuclei of the cells have undergone a mitotic remodeling, which conferred to the nucleus the ability to adapt themselves to the early embryonic development.

The present invention particularly relates to nuclei of cells of pluricellular organisms as defined above, which are nuclei of somatic differentiated cells.

In a preferred embodiment of the invention, the above-mentioned nuclei are nuclei of cells of vertebrates, chosen among mammals, in particular humans, birds, reptiles and amphibians, and particularly *Xenopus*.

In another embodiment, the present invention relates to cells of pluricellular organisms, possibly permeabilized, containing a female germinal cell (egg) extract of pluricellular organisms in M-phase of the cell cycle.

The present invention particularly relates to cells of pluricellular organisms, possibly permeabilized, which were reprogrammed by a female germinal cell (egg) extract of pluricellular organisms in M-phase of the cell cycle.

The term "reprogrammed" means that the said nuclei of said cells have undergone a mitotic remodeling, which conferred to the nucleus the ability to adapt themselves to the early embryonic development.

The present invention particularly relates to cells of pluricellular organisms as defined above, which cells are somatic differentiated cells.

In a preferred embodiment, the invention relates to cells of pluricellular organisms as defined above, which are cells of vertebrates, chosen among mammals, in particular humans, birds, reptiles and amphibians, and particularly *Xenopus*.

The present invention also relates to a process for preparing nuclei as defined above, wherein nuclei of cells of pluricellular organisms, possibly permeabilized, are in contact with a female germinal cell (egg) extract of pluricellular organisms in M-phase of the cell cycle, which allows obtaining a mitotic remodeling of the chromosomes conferring to the nucleus the ability to reproduce a replication phase characteristic of the early embryonic development.

The term "in contact" means that the nuclei and the female germinal extract are present together in suitable conditions, particularly in a medium comprising 10 mM HEPES pH 7.7, 100 mM KCl, 0.1 mM CaCl$_2$, 1 mM MgCl$_2$, 5% Sucrose, at a temperature preferably comprised from 20° C. to 23° C., and preferentially for at least 45 minutes.

The invention also relates to a process for preparing cells as defined above, wherein cells of pluricellular organisms, possibly permeabilized, are in contact with a female germinal cell (egg) extract of pluricellular organisms in M-phase of the cell cycle, which allows obtaining a mitotic remodeling of the chromosomes, conferring to the nucleus of said cells the ability to reproduce the early embryonic development.

The term "in contact" means that the cells and the female germinal extract are present together in suitable conditions, particularly in a medium comprising 10 mM HEPES pH 7.7, 100 mM KCl, 0.1 mM CaCl$_2$, 1 mM MgCl$_2$, 5% Sucrose, at a temperature preferably comprised from 20° C. to 23° C., and preferentially for at least 45 minutes.

In another embodiment, the present invention relates to a process for cloning donor cells of pluricellular organisms comprising the following steps:
- a female germinal cell (egg) extract of pluricellular organisms in M-phase of the cell cycle is in contact with
- nuclei of donor cells, possibly permeabilized, of non-human pluricellular organisms intended for the cloning, or with donor cells, possibly permeabilized, of non-human pluricellular organisms intended for the cloning,
- which allows a mitotic remodeling of the chromosomes of the aforesaid donor cells,
- the possible activation of the nuclei of the aforesaid donor cells to trigger the S-phase of the cell cycle,
- a possible step of partial or total remove of the female germinal cell (egg) extract of pluricellular organisms, particularly by washing the aforesaid nuclei or the aforesaid donor cells,
- the introduction of the nuclei or of the donor cells resulting from the previous step in an enucleated egg.

In the context of the invention, the term "cloning" means obtaining an entire animal from the nuclei of a donor cell.

The nuclei of the donor cells can be activated to trigger the S-phase of the cell cycle, in order to initiate the first divisions of the early embryonic development. The activation may be achieved by the techniques well known in the art.

The female germinal cell (egg) extract can be partially or totally removed, particularly by washing the aforesaid nuclei or the aforesaid donor cells, for example by several washings in Phosphate Buffer Saline (PBS).

The nuclei of the donor cells are introduced in an enucleated egg, according to the techniques well known in the art, such as microinjection.

For each enucleated egg, one nucleus or one donor cell is introduced.

The enucleated egg preferentially originates from the same species as the nuclei. The enucleated egg is obtained by techniques well known in the art.

The enucleated egg containing the nuclei can then be transferred in a female breeder, so as to perform its early-embryonic, embryonic and foetal development.

The present invention relates to a process as defined above, wherein the cells of pluricellular organisms are differentiated somatic cells or cells originating from different tissues of an organism.

Said cells originating from different tissues of an organism can particularly be chosen among cells originating from any kind of tissue, such as skin, intestine, liver, blood, muscle, etc.

The present invention particularly relates to a process as defined above, wherein the pluricellular organisms are vertebrates chosen among mammals, birds, reptiles and amphibians, and particularly *Xenopus*.

The invention also relates to a process for preparing nuclei of cells of pluricellular organisms, particularly vertebrates, comprising:
- a step wherein nuclei of cells of pluricellular organisms, particularly vertebrates, are in contact with a female germinal cell (egg) extract of pluricellular organisms, particularly vertebrates, in M-phase of the cell cycle, to obtain nuclei containing the female germinal cell (egg) extract, said nuclei being capable of reproducing the replication phases characteristic of the early embryonic development, and
- a step of partial or total remove of the aforesaid female germinal cell (egg) extract.

In a particular embodiment, the invention relates to nuclei of cells of pluricellular organisms, particularly vertebrates, as obtained by the implementation of the above-mentioned process.

The present invention also relates to a process for preparing cells of pluricellular organisms, particularly vertebrates, comprising:
- a step wherein cells of pluricellular organisms, particularly vertebrates, are in contact with a female germinal cell (egg) extract of pluricellular organisms, particularly vertebrates, in M-phase of the cell cycle, to obtain cells containing the female germinal cell (egg) extract, the nuclei of said resulting cells being capable of reproducing the replication phases characteristic of the early embryonic development, and
- a step of partial or total remove of the aforesaid female germinal cell (egg) extract.

In another embodiment, the present invention relates to cells of pluricellular organisms, particularly vertebrates, as obtained by the implementation of the above-mentioned process.

The invention also relates to a process for obtaining multipotent or totipotent stem cells of pluricellular organisms, particularly vertebrates, comprising the following steps:
- a female germinal cell (egg) extract of pluricellular organisms in M-phase of the cell cycle is in contact with
- nuclei of donor cells, possibly permeabilized, of non-human pluricellular organisms, or
- with donor cells, possibly permeabilized, of non-human pluricellular organisms, which allows a mitotic remodeling of the chromosomes of the aforesaid donor cells,
- the possible activation of the nuclei of the aforesaid donor cells to trigger the S-phase of the cell cycle,
- a possible step of partial or total remove of the female germinal cell (egg) extract of pluricellular organisms, particularly by washing the aforesaid nuclei or the aforesaid donor cells,
- the introduction of the nuclei or of the nuclei of the donor cells resulting from the previous step in an enucleated egg,
- a step of culturing the resulting nucleated egg in appropriate conditions for several divisions, to obtain multipotent or totipotent stem cells, and
- a possible step of culturing the resulting multipotent or totipotent stem cells in appropriate conditions to maintain said cells in an undifferentiated state.

The resulting multipotent or totipotent stem cells can be cultured in appropriate conditions to maintain said cells in an undifferentiated state.

In another embodiment, the invention relates to a process for obtaining multipotent or totipotent stem cells of pluricellular organisms, particularly vertebrates, comprising:
- a step wherein permeabilized donor cells of pluricellular organisms, particularly vertebrates are in contact with a female germinal cell (egg) extract of pluricellular organisms, particularly vertebrates, in M-phase of the cell cycle, or with an extract of non-human early embryos of vertebrates, to obtain a mitotic remodeling of the chromosomes of the aforesaid cells and to obtain the aforesaid donor cells as multipotent or totipotent cells, a possible step of partial or total remove of the aforesaid female germinal cell (egg) extract or of the aforesaid embryo extract, a possible step allowing to close up the membrane of the aforesaid multipotent or totipotent cells, and a possible step of culturing the aforesaid resulting multipotent or totipotent stem cells in appropriate conditions to maintain said cells in an undifferentiated state.

The donor cells are preferentially lightly permeabilized.

"Lightly permeabilization" is obtained for example by using low concentrations of detergent like NP40, Triton X100, Lysolecithin, digitonin.

By the expression "extract of non-human early embryos of vertebrates", it is meant an extract such as obtained by the process described in Lemaitre et al. 1998.

The invention particularly relates to a process for obtaining cells, cellular lines or tissues of pluricellular organisms, particularly vertebrates, at the desired stage of differentiation, comprising:

a step wherein permeabilized donor cells of pluricellular organisms, particularly vertebrates are in contact with a female germinal cell (egg) extract of pluricellular organisms, particularly vertebrates, in M-phase of the cell cycle, or with an extract of non human early embryos of vertebrates, to obtain a mitotic remodeling of the chromosomes of the aforesaid donor cells and to obtain the aforesaid donor cells as multipotent or totipotent cells, a possible step of partial or total remove of the aforesaid female germinal cell (egg) extract or of the aforesaid embryo extract, a step allowing to close up the membrane of the aforesaid multipotent or totipotent cells, and a step of culturing the aforesaid resulting multipotent or totipotent stem cells in appropriate conditions to obtain cells, cellular lines or tissues, at the desired stage of differentiation.

The invention also relates to cells, cellular lines or tissues as obtained by the implementation of the above defined process.

The Inventors have investigated the factors that control the ability of differentiated adult cell nuclei to participate in early developmental events when transplanted into eggs or egg extracts. In particular, the Inventors show that mitosis is crucial for resetting the nuclear organization of differentiated nuclei and for adapting them for the accelerated DNA replication of early embryos. In both metaphase-arrested *Xenopus* egg extracts and at mitosis of early embryonic cycles, the formation of mitotic chromosomes is a necessary step in organizing DNA for subsequent replication. Incubating differentiated adult nuclei in a mitotic extract shortens the average size of replicons and chromatin loop domains to those typical of endogenous chromatin present during early development. Molecular DNA combing demonstrates that a single mitosis is both necessary and sufficient to reset inter-origin spacing. This reprogramming of replicon organization is topoisomerase II-dependant, and results in an increased recruitment of replication factors to origins that is not simply a function of the amount of available pre-replication complex proteins. Finally, the Inventors show that an equivalent remodeling of the chromatin occurs at mitosis of each cell cycle during early development. These results can explain how the egg is able to remodel differentiated nuclei, and why cloning experiments by nuclear transfer of differentiated nuclei have such a high failure rate.

FIGURES

FIG. 1: Exposure to M-Phase Conditions Makes Erythrocyte Nuclei Fully Competent for DNA Replication FIG. 1A: Scheme of the experimental procedure described in the text.

Figure 1B:
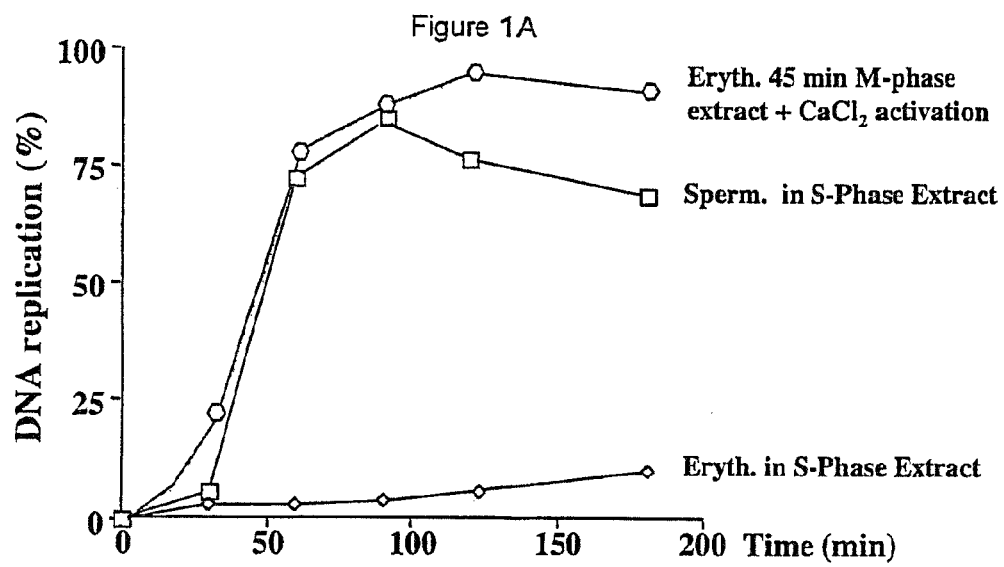

FIG. 1B: Permeabilized erythrocyte nuclei were incubated in S-phase or M-phase extract for 45 minutes before $CaCl_2$ activation to trigger S phase. 5 µl samples were taken at different times. DNA replication was monitored by TCA precipitation of $^{32}P\alpha dCTP$ incorporated into DNA and expressed as the percentage replicated DNA compared to the total input DNA. Sperm nuclei incubated in S-phase extract were used as a control. Other independent experiments show that permeabilization was not necessary when erythrocyte nuclei are incubated in M-phase extracts.

Figure 1C:
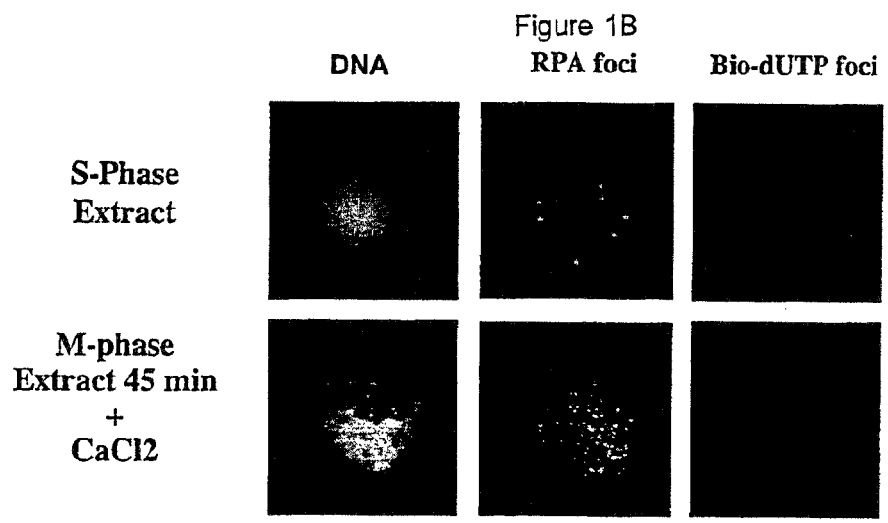

FIG. 1C: Replication initiation foci were analyzed in erythrocyte nuclei by incorporating Biotin16-dUTP in the presence of 5 µg/ml aphidicolin, as indicated, in S-phase extract or in M-phase extract for 45 minutes before $CaCl_2$ activation. DNA was stained with Hoechst 33258. The RPA antibody was revealed with an anti-mouse FITC, and Biotin-16 dUTP with streptavidin Texas red.

FIG. 2: Single molecule analysis of the inter origin spacing by molecular combing.

Sperm nuclei (FIG. 2A) and permeabilized erythrocytes nuclei (FIG. 2B) were incubated for 75 min in S-phase extract supplemented with 5 µg/ml aphidicolin and 40 µM BrdUTP. Erythrocyte nuclei (FIG. 2C) and sperm nuclei (FIG. 2D) were first incubated in M-phase extract for 45 min before CaCl2 activation and addition of aphidicolin.

Fibers were combed on silanized coverslips and the center to center distances between adjacent BrdU tracks were measured. The center to center distance between BrdU tracks is indicated in Kbp. Lower panel, BrdU; upper panel, merge BrdU/DNA.

FIG. 3: Histone acetylation does not induce erythrocyte nuclei remodeling.

FIG. 3A: Sperm nuclei were incubated in S-phase extract in the presence of histone acetylation activators (300 µM TSA and 300 µM CTPB).

FIG. 3B: Sperm nuclei were incubated in S-phase extract in the presence of a histone acetylation inhibitor (300 µM AA). A prior incubation of 600 µM CTPB was necessary to prevent inhibition of DNA replication by 300 µM AA.

FIG. 3C: Permeabilized erythrocyte nuclei were incubated in S-phase extract containing either 300 µM TSA, 600 µM CTPB, or 300 µM AA. Sperm nuclei incubated in S-phase extract were used as a control.

FIG. 3D: Transfer of sperm and erythrocyte chromatin from a 45 min incubation in M-phase extract to S-phase extract containing 300 µM AA.

5 µl samples were taken at different times and DNA replication was monitored by TCA precipitation of $^{32}P\alpha dCTP$ incorporated into DNA.

FIG. 4: Mitosis-Induced Remodeling of Nuclear Organization

Figure 4A:
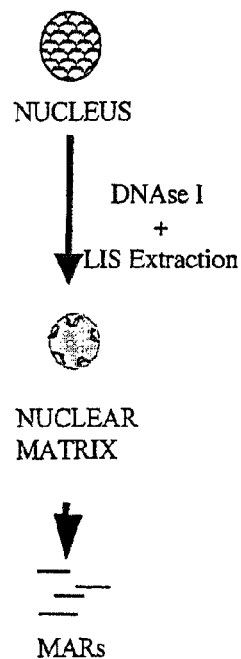

FIG. 4A: Erythrocyte nuclei were incubated either in S-phase or M-phase egg extract or mock incubated. The nuclear matrix-associated DNA was purified using the LIS procedure and the DNA fragments remaining on the matrix were $^{32}$P-labelled and used to probe specific regions of the rDNA domain.

Figure 4D:
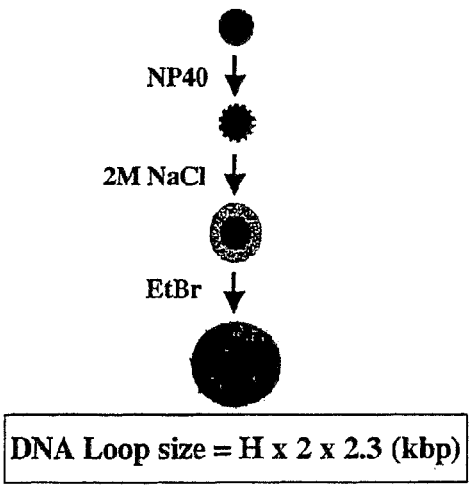
Figure 4E:
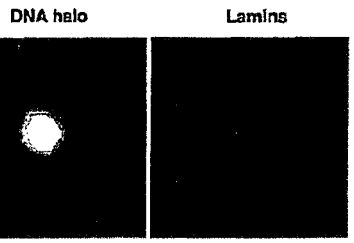
Figure 4B:
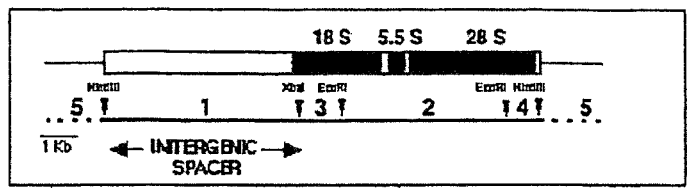

FIG. 4B: A plasmid containing the *Xenopus* rDNA domain was cut with HindIII, EcoRI, and XbaI to produce five fragments. Fragment 1 is the intergenic spacer element between the rDNA units, Fragments 2, 3 and 4 are within the transcription unit, and Fragment 5 is the vector sequence.

Figure 4C:
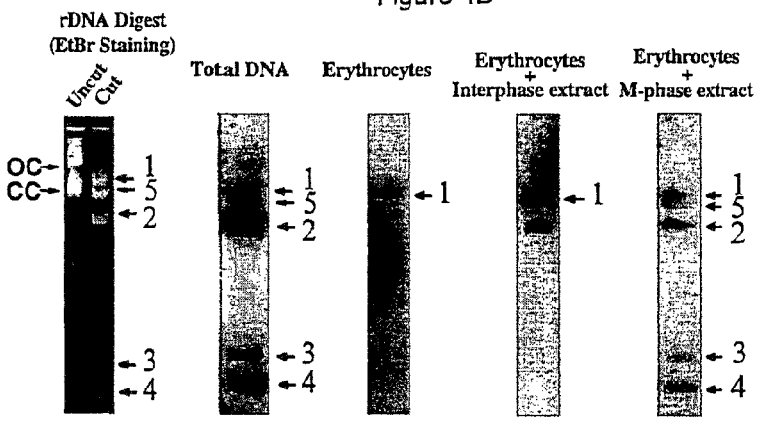

FIG. 4C: DNA fragments were separated by agarose gel electrophoresis and stained with Ethidium Bromide (first gel) or transferred to nylon membranes for hybridization. Total *Xenopus* DNA often partly hybridizes with one of the plasmid bands (second gel), as does the matrix-associated DNA from erythrocytes incubated in M-phase extract (fifth gel), emphasizing the random nature of this fraction. Hybridization of the rDNA digest with matrix attachment fraction is shown from erythrocytes incubated (4) or not (3) in S-phase egg extract.

FIG. 4D: Nuclei were recovered on coverslips and submitted to the maximum fluorescent halo technique (MFHT) for DNA loop size measurements (Material and Methods).

FIG. 4E: Ethidium bromide was used to stain DNA loops as in FIG. 4D, while immunostaining with anti-lamin antibody was also used to delimitate matrix and loop fractions.

Figure 4F:
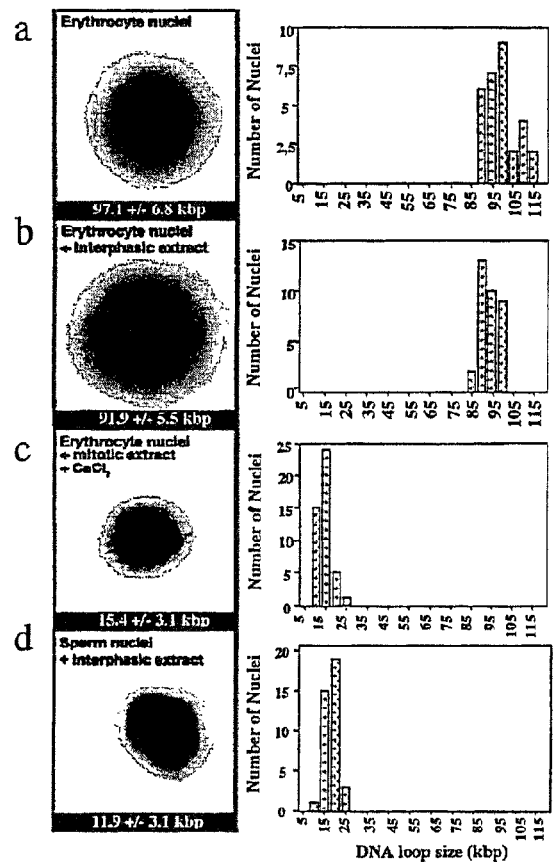

FIG. 4F: The method was applied to both sperm nuclei and erythrocyte nuclei in interphase that had been previously incubated for 45 min in M-phase egg extract. Histograms show individual loop size measurements.

FIG. 5: ORC Binding and DNA Replication Efficiency Depends on the Chromatin Context and on Topoisomerase II Activity.

FIG. 5A: Erythrocyte chromatin was incubated either in M-phase extract and immediately driven into S phase by $Ca^{++}$, or in M-phase extract for 45 min before induction into S phase by $Ca^{++}$ in the absence or presence of ICRF. Control sperm chromatin in M-phase extracts induced to enter S phase by calcium is shown. The amount of nuclei was 1000 nuclei/µl egg extract for sperm nuclei, and 500 nuclei/µl egg extract for erythrocyte nuclei to keep the chromatin concentration constant.

FIG. 5B: Demembranated erythrocyte nuclei or sperm nuclei were incubated in a mitotic egg extract in the presence or absence of 50 µg/ml of the topoisomerase II inhibitor ICRF193. DNA was stained with Hoechst dye for chromosome formation analysis.

FIG. 5C: Chromatin was purified and proteins analyzed by SDS gel electrophoresis as described in Material and Methods. Erythrocyte nuclei (500 nuclei/µl egg extract) or sperm nuclei (1000 nuclei/µl egg extract) were incubated in a mitotic egg extract, induced to enter S phase with calcium, in the presence (+) or absence (−) of ICRF 193. Chromatin was purified 30 min after calcium activation and analyzed by immunoblot with a *Xenopus* anti ORC2 antibody.

FIG. 5D: Sperm nuclei and erythrocyte nuclei were incubated for 30 min in S-phase extract at various DNA concentrations. Chromatin was purified and analyzed by 10% SDS PAGE by immunoblot with a *Xenopus* anti ORC2 antibody.

FIG. 5E: Quantitation from the immunoblot of FIG. 5D.

FIG. 6: Cell Cycle Remodeling of Chromatin Organization in Early *Xenopus* Embryos.

Figure 6A:
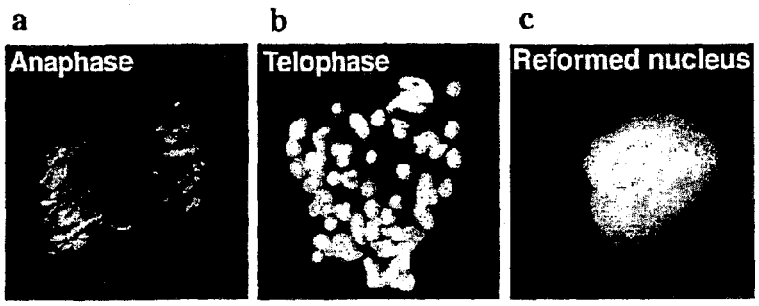

FIG. 6A: Karyomeres form at the anaphase-telophase transition and initiate DNA replication before nuclei are reconstructed (Lemaitre et al, 1998). DNA was stained with Hoechst 33258 and embryonic nuclei at anaphase (a), telophase (b) and after replication (c) are shown.

Figure 6B:
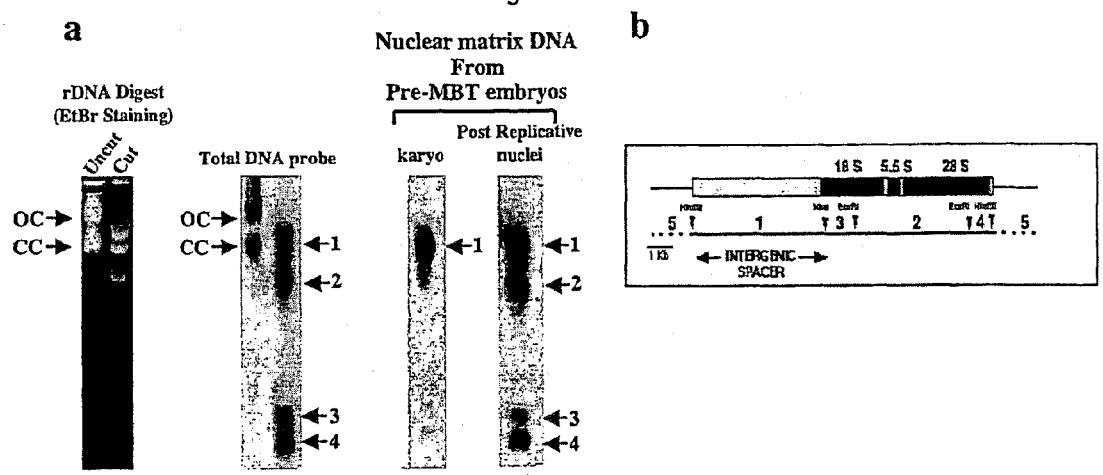

FIG. 6B: Nuclei from early embryos were isolated and treated with DNase I. The nuclear matrix was prepared using the LIS procedure (Materials and Methods) and the DNA fragments remaining on the matrix were 32P-labelled and used to probe for specific regions of the rDNA domain as in FIG. 4. The fragments were separated by agarose gel electrophoresis and stained with Ethidium bromide, or transferred to nylon membranes and hybridized either with total *Xenopus* DNA probe or with nuclear matrix DNA from karyomeres or early embryonic post-replicative nuclei.

Figure 6C:
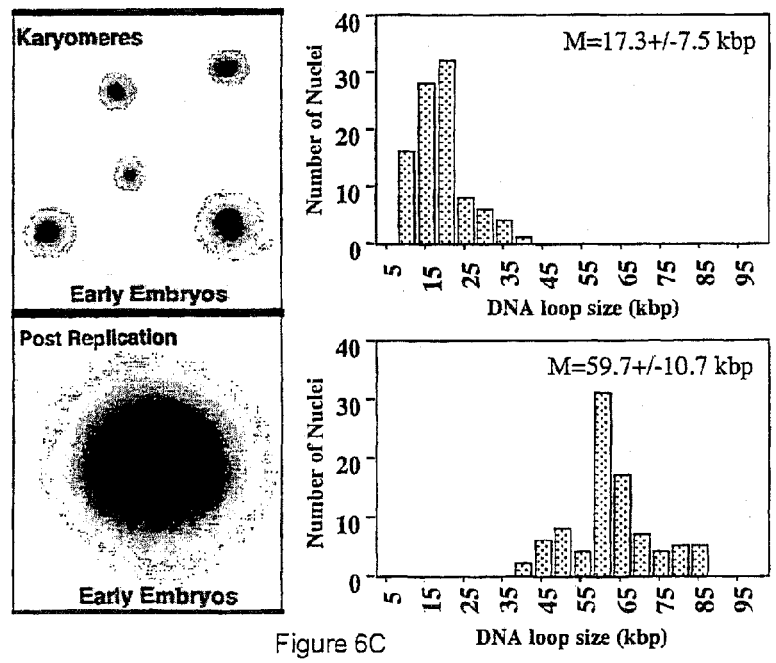

FIG. 6C: Nuclei were recovered on coverslips and submitted to the maximum fluorescent halo technique (MFHT). Histograms show individual loop size measurements.

FIG. 7: Mitotic Remodeling of Chromatin Loop Domains Occurs in S and M-Phases.

FIG. 7A: Sperm nuclei or post-replicative nuclei were incubated in S-phase extract in the presence of $^{32}$PαdCTP. 5 µl samples were taken at different times and DNA replication was quantitated by TCA precipitation.

FIG. 7B: The length of nascent DNA strands analyzed by 0.8% agarose alkaline gel electrophoresis The position of molecular weight markers (MW) run in parallel is indicated.

FIG. 7C: Sperm nuclei collected at different times during replication or following M-phase were recovered on coverslips and submitted to MFHT for DNA loop size measurements. Entry into mitosis was induced by incubating post-replicate embryo nuclei in M-phase extract in the presence or absence of ICRF.

FIG. 7D: Distribution of loop sizes.

Figure 8:
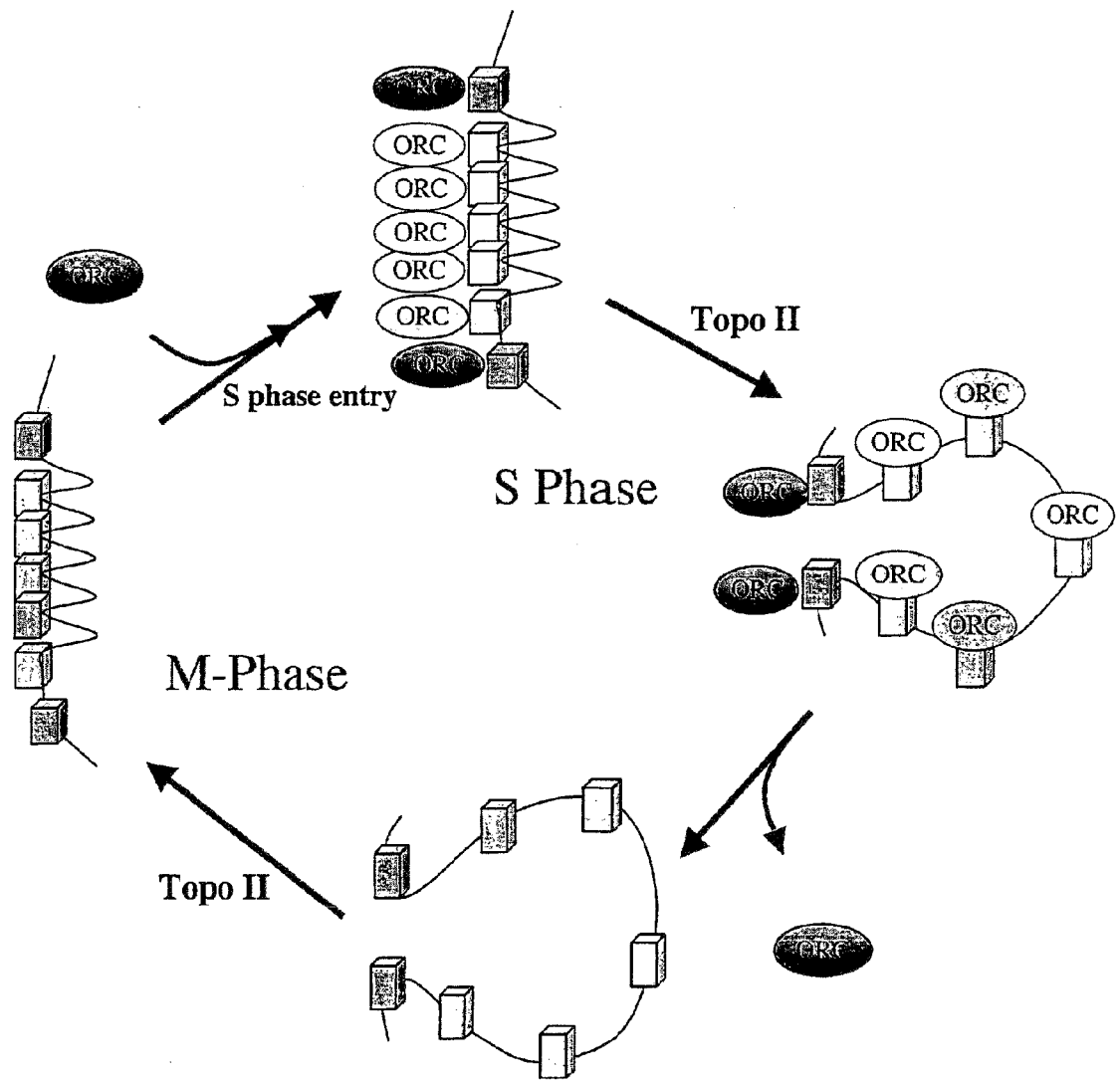

FIG. 8: Cell Cycle Remodeling of Chromatin Organization in the Early *Xenopus* Embryo.

Reorganization of chromatin occurs with each cell cycle and is dependent on Topo II activity. During S-phase, fusion of replicons leads to an increase in the mean DNA loop size. These large loops are remodeled into small loops at each mitosis and permit an increased binding of ORC for a higher rate of DNA replication. Border (dark) and internal (light) boxes of FIG. 8 represent both potential loop attachment sites and replication origins.

FIG. 9: Pre-RC Proteins and Nucleosome Assembly in M-Phase.

Figure 9A:
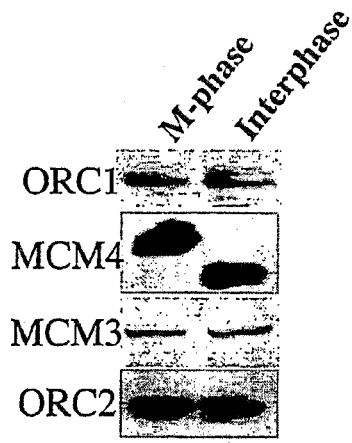

FIG. 9A: One microliter of extract was loaded onto a 10% SDS PAGE and transferred for immunoblotting with ORC1, ORC2, MCM3 and MCM4 antibodies. Note the dephosphorylation of MCM4 at mitosis exit, as previously described (Coue et al., 1996).

Figure 9B:
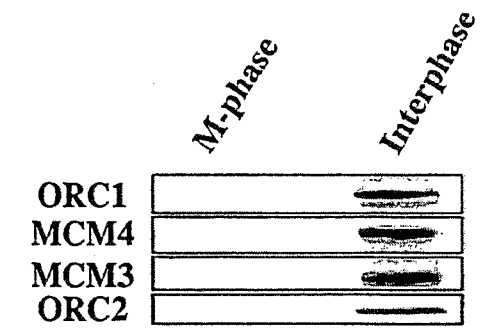

FIG. 9B: Chromatin assembled in M-phase or S-phase extract was purified as described in Materials and Methods and analyzed for ORC1, ORC2, MCM4, and MCM3 binding.

Figure 9C:
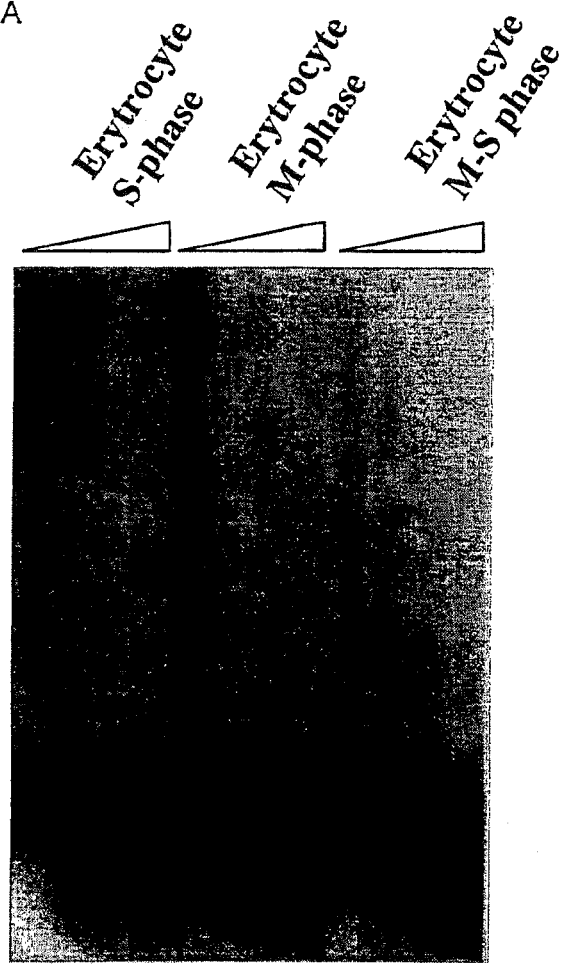

FIG. 9C: Nucleosome spacing assay: Chromatin was purified from erythrocytes, incubated either in S-phase extract or for 45 min in M-phase extract before S-phase triggering with $CaCl_2$, and resuspended in micrococcal digestion buffer containing 0.3% Triton X-100 and 3 mM $CaCl_2$. Chromatin digestion was initiated by adding 60 U micrococcal nuclease, as described (Almouzni and Mechali, 1988), and DNA products were analyzed by 1.8% agarose gel electrophoresis. A ladder of nucleosomes was observed in both cases.

FIG. 10: Chromatin Organization in the rDNA Domain Revealed Using DNA Arrays.

A recently-developed method for mapping the interactions of DNA with the nuclear matrix based on oligonucleotide DNA arrays (Ioudinkova et al., 2005) was used to confirm the results presented in FIG. 4.

FIG. 10A: rDNA gene domain. Numbered blocks indicate the positions of the oligonucleotides within the array.

FIG. 10B: The graphs represent the hybridization ratios of nuclear matrix-associated DNA normalized against an internal oligonucleotide no. 1. The average of two independent experiments is presented. Total *Xenopus* DNA hybridized equally to the rDNA array, suggesting that the chosen oligonucleotides do not contain external DNA repeats.

Figure 11:
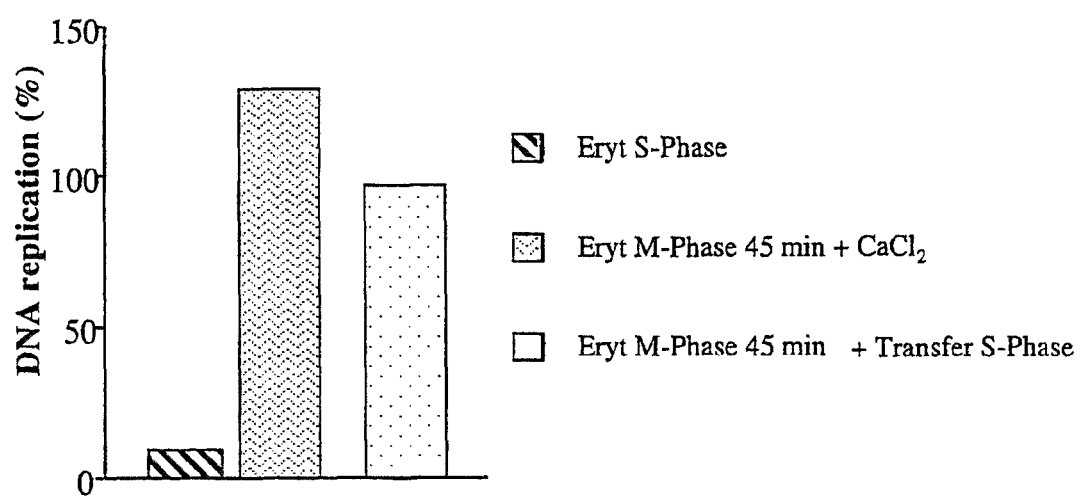

FIG. 11: Erythrocyte Remodeling Does Not Occur During the Transition from M to S phase.

Erythrocytes nuclei were incubated for 45 min in M-phase extract and chromatin purified without previous activation of the M-phase extract. It was then directly transferred to S-phase extract. DNA replication was measured by a 3 hours incubation in S-phase extract in the presence of $^{32}P\alpha dCTP$. The first control corresponds to the level of replication obtained with erythrocyte incubated in the same conditions in M-phase extract during 45 min and ca2+ activated to trigger S phase. The second control corresponds to the level of replication of erythrocytes nuclei incubated directly in S-phase extract without M-phase remodeling.

Figures 12A, 12B:
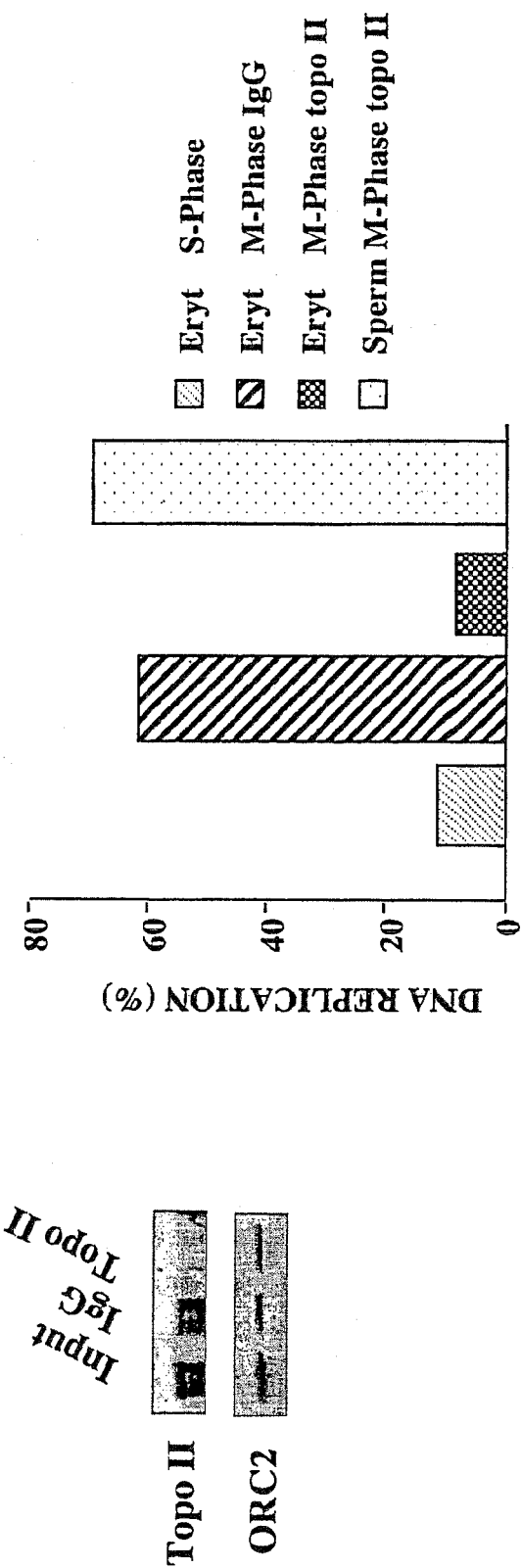

FIG. 12: Topo II Depletion in M-Phase Extract Prevents Mitotic Remodeling of Eerythrocyte Nuclei FIG. 12A: Depletion of TopoII in M-phase was carried out using an anti-TopoII polyclonal antibody kindly provided by Dr. Bogenhagen. Depletion was monitored by immunoblot.

FIG. 12B: Erythrocyte nuclei and sperm nuclei were incubated in a depleted M-phase extract for 45 min and S-phase was triggered by addition of $CaCl_2$. DNA replication was measured after 3 hours of incubation. A mock depletion was also performed using a non-specific rabbit IgG.

Figure 13:
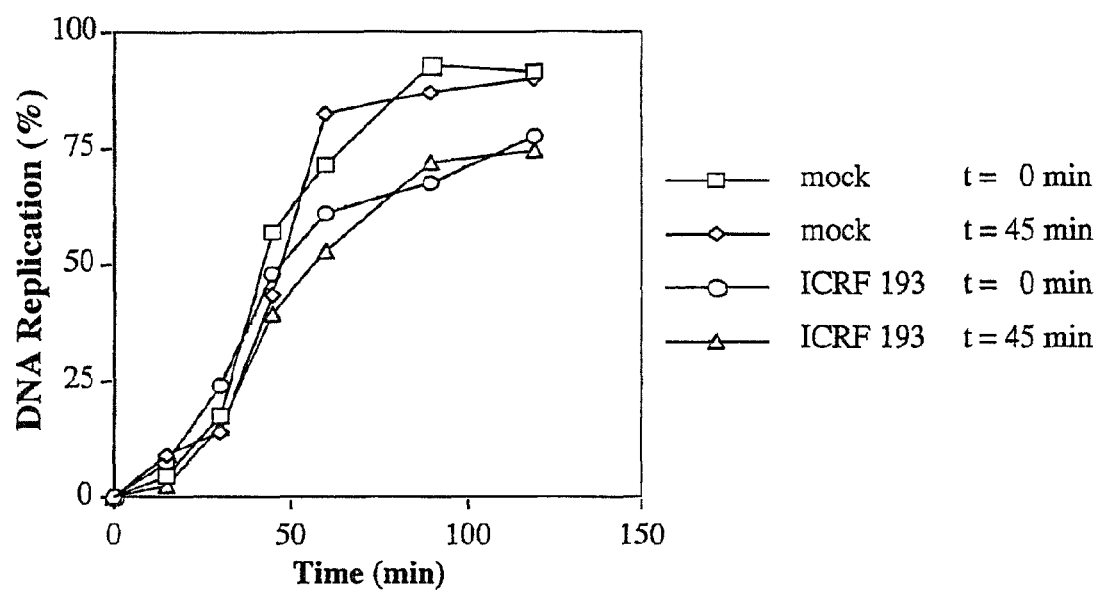

FIG. 13: Topo II Inhibition of S Phase Extracts by ICRF193 Does Not Interfere with DNA Replication Sperm chromatin was incubated in S-phase extract in the presence of 50 µg/ml ICRF193 at the beginning of the reaction or after 45 min (during the elongation phase). DNA replication was monitored by TCA precipitation of the replicated DNA.

FIG. 14: Replicon and ORC2 Binding in Sperm Nuclei or Post-Replicative Embryonic Nuclei.

Figure 14A:
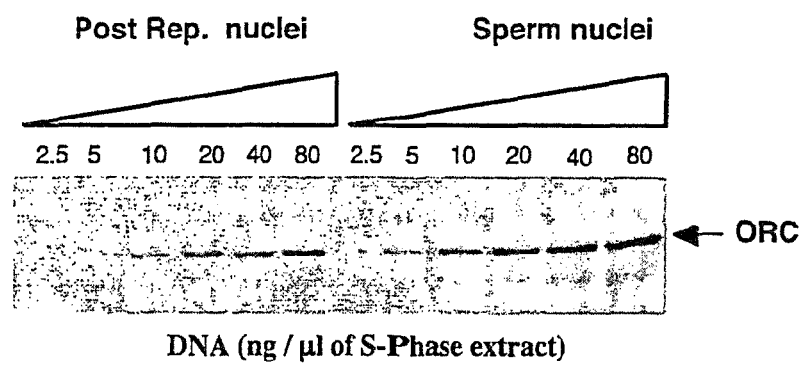

FIG. 14A: Demembranated post-replicative embryonic nuclei or demembranated sperm nuclei were incubated in S-phase extract. Chromatin was purified and proteins analyzed by SDS gel electrophoresis as described in Material and Methods.

Figure 14B:
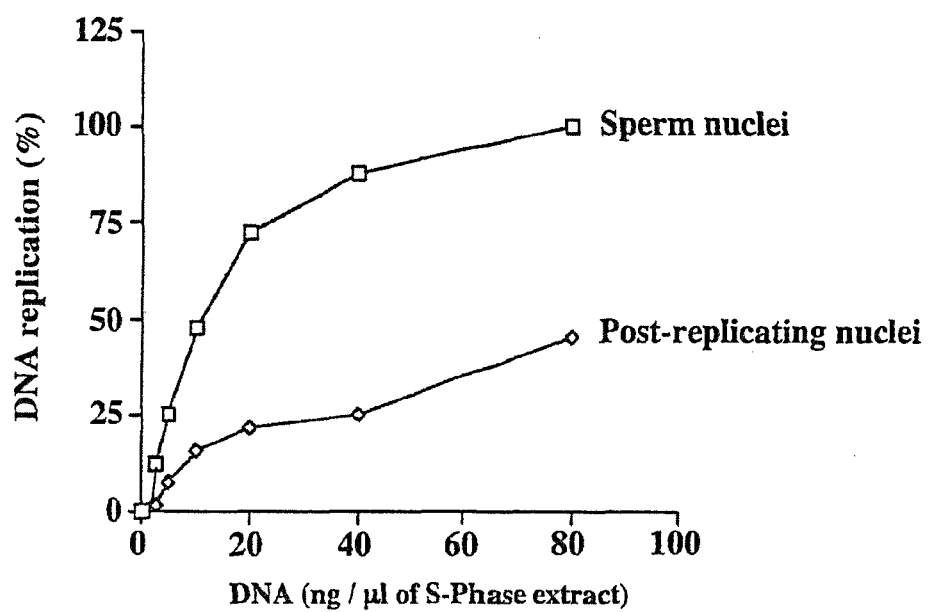

FIG. 14B: Quantitation from the immunoblot.

EXAMPLES

Example 1

Mitotic Remodeling of Replicon

Nuclear transfer experiments frequently fail due to the inability of most transplanted nuclei to support normal embryonic development. The Inventors show here that the formation of mitotic chromosomes in the egg context is crucial for adapting differentiated nuclei for early development. Fully-differentiated erythrocyte nuclei replicate inefficiently in Xenopus eggs, but do so as rapidly as sperm nuclei if a prior single mitosis is permitted. Formation of chromosomes is necessary and sufficient to reset erythrocyte nuclei to short inter-origin spacing characteristic of early developmental stages. This resetting involves a shortening of chromatin loop domains and an increased recruitment of replication initiation factors onto chromatin, leading to a large increase in replication origins. Finally, the Inventors show that this mitotic remodeling is topoisomerase II dependent, occurs with each early embryonic cell cycle, and dominantly regulates the initiation of DNA replication at the subsequent S phase. These results indicate that mitotic conditioning is determinant to reset chromatin structure of differentiated adult donor cells for embryonic DNA replication, and suggest that it is an important step in nuclear cloning.

Material and Methods

Xenopus Egg Extracts and Early Embryos

S-Phase and M-phase low speed (LS) extracts were prepared according to protocols described in detail by (Menut et al., 1999) and available at www.igh.cnrs.fr/equip/mechali/. Embryos were grown in 0.1× Barth's medium as described (Lemaitre et al., 1995). To obtain karyomeres, perfectly synchronized embryos were selected at each division over the first four divisions. Embryos were then taken at the fifth division when the furrow appears. Subsequent divisions give rise to metasynchronous divisions in the embryos. G2-like synchronized embryos were obtained by 45 min incubation in 0.1× Barth's medium containing 150 µg/ml cycloheximide between the 32- and 64-cell stages and between the 512- and 1,024-cell stages. Embryos were dejellied with 2% cysteine HCl, pH 7.9, and homogenized through a 1-ml Gilson tip before centrifuged at 4° C. for 10 min at 10,000 g. Under these conditions, the endogenous embryonic nuclei (karyomere or reformed nuclei) remain in the supernatant (Lemaitre et al., 1998).

Replication Reactions

Demembranated sperm nuclei were prepared and used as described in (Menut et al., 1999), and erythrocyte nuclei were purified from Xenopus blood as described. Nuclei were incubated in S-phase (1,000 nuclei/µl), or M-phase (CSF) extracts that were activated with 1 mM $CaCl_2$. DNA synthesis was measured by $^{32}P$-dCTP incorporation, as previously described (Menut et al., 1999).

Purification and Analysis of Chromatin Fractions

50 µl samples were diluted with 5 volumes of extract buffer (XB: 100 mM KCl, 0.1 mM $CaCl_2$, 1 mM $MgCl_2$, 10 mM KOH-Hepes pH 7.7, 50 mM sucrose) and pelleted by centrifugation at 7500 g for 12 min through a 0.7 M sucrose cushion. Nuclear pellets were resuspended in XB, 0.3% Triton X-100 and incubated for 5 min on ice. After a further 5,000 g centrifugation for 5 min, chromatin pellets were recovered and adjusted in Laemmli Buffer.

Antibodies

Lamins were visualized with the 687A7 antibody (Firmbach-Kraft and Stick, 1995). The anti-RPA34-specific monoclonal antibody (324A.1) was used as described (Francon et al., 2004). The rabbit polyclonal antibody against Cdc6 was produced as described (Lemaitre et al., 2002). Antibodies against Cdt1 and MCM4 were obtained by four injections of corresponding recombinant proteins. Other antibodies were generous gifts from J. Walter (ORC2), and D. Bogenhagen (TopoII).

Immunocytochemistry

Extracts containing nuclei were diluted 10-fold in 100 mM KCL, 50 mM sucrose, 5 mM $MgCl_2$, 0.5 mM EDTA, 20 mM Hepes pH 7.6, and nuclei were purified through a 0.7 M sucrose cushion. Alternatively, samples were directly fixed with an equal volume of XB containing 4% formaldehyde and 1 µg/ml Hoechst 33258. Rehydration was done in PBS. Isolated nuclei were incubated for 1 hour at room temperature in PBS 2% BSA, 0.1% Tween 20 to block non-specific interactions. Incubation with specific antibodies was carried out overnight at 4° C. in PBS, 2% BSA. After several washes, the second FITC-conjugated or Texas Red-conjugated streptavidin was added following instructions from the manufacturers. To reveal Biotin dUTP, FITC or Texas Red conjugated-streptavidin was mixed with the second antibody at the appropriate dilution. DNA was stained with 1 µg/ml Hoechst 33258.

DNA Combing

Nuclei embedded in agarose plugs (800 ng DNA/plug) were stained with YOYO-1 (Molecular Probes) and resuspended in 50 mM MES pH 5.7 (150 ng/ml) after digestion of the plugs with agarase (Roche). DNA combing was performed as described (Michalet et al., 1997). Combed DNA fibers were denatured for 30 min with 1 N NaOH and BrdU was detected with a rat monoclonal antibody (Sera Lab) and a secondary antibody coupled to Alexa 488 (Molecular Probes). DNA molecules were counterstained as previously described (Versini et al., 2003) with an anti-guanosine antibody (Argene) and an anti-mouse IgG coupled to Alexa 546 (Molecular Probes). Center-to-center distances between BrdU tracks were measured with MetaMorph (Universal Imaging Corp.) using adenovirus DNA molecules as a size standard (1 pixel=680 bp).

Loop Size Measurement

Maximum Fluorescent Halo Radius (MFHR) were determined by treating non-fixed nuclei on coverslips. They were first dipped for 1 min in ice cold NP40 buffer (0.5% NP40, 10 mM $MgCl_2$, 0.5 mM $CaCl_2$, 50 mM Hepes pH 7.8) and then sequentially dipped for 30 s in a solution containing 0.2 mM $MgCl_2$, 10 mM Tris (pH 7.4) with 0.5 M, 1 M, 1.5 M, 2 M NaCl. They were then incubated in 100 µg/ml ethidium bromide, 2 M NaCl and exposed for 1 min to short wave UV light before observation by fluorescence (Buongiorno-Nardelli et al., 1982). Halo and matrix diameters were estimated using a micrometrics slide. DNA loop size was calculated taking into account that the loop size is 2 fold the MFHR. The length of linear DNA was calculated using the correspondence of 1 µm to 2.3 kbp.

Analysis of DNA Loop Attachments Sites

Nuclear matrices were prepared by treating isolated nuclei with restriction endonucleases or DNase I followed by extraction with either Lithium 3,5-diiodosalicylate (LIS) or 2 M NaCl, essentially as described in (Gasser and Laemmli, 1986; Vassetzky et al., 2000). Nuclei were digested with 100 µg/ml DNaseI for 3 h at 0° C. in (100 mM NaCl, 25 mM KCl, 10 mM Tris-HCl, pH 7.5, 0.25 mM spermidine, 1 mM $CaCl_2$). The digestion was followed by a stabilization step, the addition of $CuCl_2$ to a final concentration of 1 mM, and incubation for 10 min at 4° C. The nuclei were extracted with five volumes of LIS extraction buffer containing 10 mM Tris-HCl, pH 7.5, 0.25 mM spermidine, 2 mM EDTA-KOH, pH 7.5, 0.1% digitonin, and 25 mM LIS for 5 min at room temperature. The histone-depleted nuclear matrices were recovered by centrifugation at 2,500 g for 20 min at room temperature, and the nuclear matrix pellet was washed three times in 20 mM Tris-HCl, pH 7.5, 0.25 mM spermidine, 0.05 mM spermine, 100 mM NaCl, and 0.1% digitonin. The size range of the nuclear matrix-attached DNA was 400-1500 bp.

Oligonucleotide DNA Array

The array was devised to use the complete Xenopus rDNA sequence, assembled from entries X05264 and X02995 (Genbank) and comprising 11505 base pairs. The micro-array consisted of seven oligonucleotides spaced approximately 1500 bp apart (see Table 1) and possessing similar sizes (25-30 bp) and annealing temperatures (60±1°). The first two oligonucleotides covered the intergenic spacer and the other five spanned the 40S transcript.

The oligonucleotides were slot-blotted onto Zeta-probe GT filters in 0.4 NaOH and fixed by baking at 80° C. for 30 min. Each filter contained the array in duplicate. The hybridization was carried out at 58° C. in modified Church buffer (0.5 M phosphate buffer pH 7.2, 7% SDS, 10 mM EDTA) overnight. The blot was subsequently washed in 2×SSC, 0.1% SDS twice for 5 min, and then in 1×SSC, 0.1% SDS, twice for 10 min and exposed on a PhosphoImager. All experiments were done in duplicate. The data has been normalized versus an internal control (oligonucleotide No. 1).

TABLE 1

| Position | Oligonucleotide | Size, nt | Annealing temperature, ° C. |
|---|---|---|---|
| 1476 | GGAGAGGTAGAGACAAGACAGA GGC (SEQ ID NO: 1) | 25 | 60, 3 |
| 2723 | GGGCGAAGAAAACCGGGAGAAA TAC (SEQ ID NO: 2) | 25 | 60, 8 |
| 4136 | GAGAGAAAGACGGAAAGAAAGG AGAGTAG (SEQ ID NO: 3) | 29 | 60 |
| 5279 | CATTCGTATTGTGCCGCTAGAG GTG (SEQ ID NO: 4) | 25 | 60, 7 |
| 7181 | CCACGACTCAGACCTCAGATCA GAC (SEQ ID NO: 5) | 25 | 60, 8 |
| 8829 | GTAACAACTCACCTGCCGAATC AACTA (SEQ ID NO: 6) | 27 | 60, 3 |
| 10262 | CTGTGAAGAGACATGAGAGGTG TAGGATAA (SEQ ID NO: 7) | 30 | 60, 9 |

Results

Reprogramming Differentiated Nuclei for DNA Replication Requires Passage through Mitosis When sperm nuclei are introduced into Xenopus interphase egg extracts, they replicate almost immediately and with an efficiency of close to 100%, similar to what happens in vivo following fertilization (Blow and Laskey, 1986). In contrast, erythrocyte nuclei replicate inefficiently (Leno and Laskey, 1991; Lu et al., 1999). Both human and Xenopus eggs are normally blocked at the stage of the second meiotic division with condensed chromosomes at the metaphase stage (Tunquist and Mailer, 2003), and fertilization induces a calcium pulse that triggers the end of mitosis and the onset of embryonic cleavage. However, when differentiated nuclei are transplanted into eggs, microinjection induces an immediate exit from mitosis and thereby prevents differentiated nuclei from undergoing mitotic chromosome condensation prior to passage into post-mitotic cell cycle phases.

The Inventors asked whether passage through mitosis might be a prerequisite for reprogramming the nucleus for rapid DNA replication. The experimental procedure outlined in FIG. 1A was used. Erythrocyte nuclei were either permeabilized and directly incubated in Xenopus S-phase extracts, or incubated in a mitotic egg extract before activation in S phase. The Inventors observed that permeabilized erythrocyte nuclei replicate less efficiently in S-phase egg extracts than do permeabilized sperm nuclei (FIG. 1B). When permeabilized erythrocyte nuclei were first, however, incubated in an M-phase extract prepared from eggs blocked at the second meiotic metaphase by EGTA (Murray, 1991) prior to S phase induction using $CaCl_2$, replication occurred as rapidly and efficiently as in sperm nuclei (FIG. 1B). The Inventors confirmed that chromosomes were formed before the $Ca^{2+}$ was added in each experiment (data not shown and FIG. 5A). In other words, the formation of chromosomes by an initial exposure to mitotic conditions made erythrocyte nuclei as competent for DNA replication as sperm chromatin. As previously seen with sperm chromatin (Adachi and Laemmli, 1992), erythrocyte DNA replication occurred in foci colocalizing with RPA (FIG. 1C); the Inventors observed an increased number of such foci when erythrocyte chromatin was allowed to first pass through mitosis.

M-Phase Extract Conditioning Increases Number of Replication Origins

While DNA replication initiates at origins spaced every 10 to 20 Kbp during early *Xenopus* development, permitting a high rate of replication (Hyrien and Mechali, 1993; Walter and Newport, 1997), in most dividing somatic cells the replicon size ranges from 50 to 300 Kbp (Berezney et al., 2000). To address whether mitotic remodeling of erythrocyte nuclei affects replicon size, the Inventors analyzed the spacing of origins by DNA combing (Michalet et al., 1997). In this method, DNA molecules are stretched uniformly, providing an accurate determination of origin density along the DNA (Pasero et al., 2002). Erythrocyte nuclei were incubated in egg extracts in the presence of BrdUTP, which labels initiation sites, and a low concentration of aphidicolin, which permits initiation but slows elongation dramatically (Walter and Newport, 2000; Wu et al., 1997; and unpublished results of the Inventors). Chromosomal DNA was purified and combed on silanized glasses, BrdU incorporation detected using anti-BrdU antibodies, and DNA fibers counter-stained with an anti-guanosine antibody. FIG. 2A shows that sperm nuclei had an average spacing of 23.4 Kbp between replication origins, while the spacing for erythrocyte nuclear chromatin incubated in S-phase egg extract ranged from 30 to 230 Kbp (FIG. 2B). 77% of the replicons were smaller than 30 Kbp in the *Xenopus* nuclei, whereas 97% of the replicons were larger than 30 Kbp in the erythrocyte nuclei. The Inventors conclude that the slow replication observed in erythrocyte nuclei that had been exposed to S-phase extract was due to a low frequency of replication initiation within the genome.

When erythrocyte nuclei were first exposed to M-phase extract before entry into S phase, however, the spacing of origins was shortened to 24.9 Kbp, similar to sperm nuclei (FIG. 2C). The proportion of replicons larger than 30 Kbp was dramatically decreased, with 74% of the replicons being in the 10-30 Kbp range. Finally, incubation of sperm nuclei in an M-phase extract prior to S phase had no effect on origin spacing (FIG. 2D). The Inventors conclude that prior conditioning of erythrocyte nuclei in M-phase extract set an origin spacing similar to those of sperm chromatin upon entry into S phase.

Mitotic Remodeling is not Due to Global Changes in Nucleosome Organization Nor to Histone Acetylation Levels Although the above results could suggest a superior ability of M-phase extract to assemble proteins of the pre-replication complex, the Inventors doubted this possibility for two reasons. First, M-phase extracts do not contain higher levels of pre-replication complex proteins than do interphase egg extracts (Supplementary FIG. 1A and unpublished results). Second, several of the proteins do not bind to chromatin during mitosis, including ORC, CDC6, Cdt1, RPA, and MCMs (Supplementary FIG. 1B).

An alternative explanation is that building mitotic chromosomal structures is sufficient to reset the nuclear organization of erythrocyte nuclei for DNA replication in the next cell cycle. To test this possibility, the Inventors first examined nucleosome assembly and spacing in the nuclei. As shown in Supplementary FIG. 1C, the global nucleosome organization was similar regardless of whether the nuclei were added directly to the S-phase extract or were first incubated in an M-phase extract.

The Inventors also investigated whether the level of histone acetylation could account for their results, particularly in view of the recent suggestion that acetylation may contribute to the specification of replication origins (Aggarwal and Calvi, 2004; Danis et al., 2004). Histone acetylation is determined by the equilibrium between the activities of histone acetyl transferases (HATs) and histone deacetylases (HDACs), both of which are present in *Xenopus* oocytes (Ryan et al., 1999; Wade et al., 1999). This equilibrium can be modified in favor of acetylation either by inhibiting deacetylases with trichostatin (TSA) or by activating acetylases with CTPB. Conversely, histone deacetylation can be promoted by inhibiting histone acetylases with anacardic acid (AA) (Balasubramanyam et al., 2003). FIG. 3A shows that favoring acetylation (TSA or CTPB) had no significant effect on the replication rate of sperm chromatin incubated in S-phase extract. These results indicated either that histone acetylation is not necessary for DNA replication of sperm nuclei, or that the level of acetylation present in the extract is sufficient to allow a maximum rate of replication. FIG. 3B shows that the latter possibility is more likely, as AA, which causes hypoacetylation of H3 and H4, strongly inhibited the replication of sperm nuclei in S-phase extract. This inhibition could be reversed by the activator CTPB. These results clearly indicate that histone acetylation is required for the rapid replication seen during early development, and that the steady-state level of acetylation activity in the egg is sufficient for a maximum rate of DNA replication.

As with sperm chromatin, the acetylation activators TSA and CTPB failed to significantly affect the replication rate of erythrocyte nuclei incubated in S-phase extract (FIG. 3C). Unlike with sperm chromatin, however, the acetylase inhibitor AA did not further inhibit the inefficient DNA replication of erythrocyte nuclei. Erythrocyte nuclei that had been remodeled in mitosis, however, were as sensitive as sperm nuclei to AA (FIG. 3D). Together, these data suggest, first, that although acetylation is required for the rapid DNA replication characteristic of early S phases, its level is sufficient for a full rate of DNA replication and therefore cannot account for the slow DNA replication rate observed with erythrocyte nuclei in interphasic extracts. Second, they indicate that the organization of erythrocyte chromatin negatively regulates DNA replication in a dominant manner in S phase extracts, unless mitotic chromosomes are first formed by incubation in an M-phase extract.

Mitotic Reorganization of Erythrocyte Chromatin Domains

The Inventors next investigated global changes in the organization of erythrocyte chromatin that could explain replicon remodeling. A transition from a random association with the nuclear matrix to a defined anchorage occurs during *Xenopus* development as chromatin domains become organized for transcription after the Mid Blastula transition (Vassetzky et al., 2000). The Inventors hypothesized that the reverse could take place when erythrocyte nuclei are exposed to egg extracts. To test this, nuclei incubated in M-phase extracts, S-phase extracts, or mock incubated, were treated with DNase I and then extracted with LIS, which removes histone and non-histone proteins but preserves the attachment sites of DNA loops to the nuclear scaffold (FIG. 4A). The DNA remaining on the matrix was isolated, labeled, and used as a probe to hybridize to agarose gel-separated regions of the rDNA domain (FIGS. 4B, 4C). The gels were also probed with total *Xenopus* erythrocyte DNA (FIG. 4C).

Each unit of the rDNA domain comprises a transcribed region and a non-transcribed spacer. A single band corresponding to the intergenic spacer was detected when matrix-associated erythrocyte DNA was used as a probe, whereas all rDNA bands were detected when total *Xenopus* erythrocyte DNA was used (FIG. 4C). While exposing erythrocyte nuclei to S-phase egg extract did not significantly alter the rDNA specificity, incubation in an M-phase egg extract produced a randomization of the attachment sites, as all rDNA domains were detected with similar efficiency (FIG. 4C). The Inventors obtained analogous results with a different method using oligonucleotide arrays. Nuclear matrix DNA from erythrocytes only hybridized to the two oligonucleotides corresponding to the intergenic spacer, confirming the results of FIG. 4. Incubation of erythrocyte nuclei in S-phase extract did not alter the hybridization pattern. Incubation of erythrocyte nuclei in mitotic extracts led to a hybridization pattern similar to that of total DNA, suggesting a lack of specific locus attachment sites. Inhibition of DNA topoisomerase II in the M-phase extract or, to a lesser extent, depletion of DNA topoisomerase II with specific antibodies, maintained the original organization of the rDNA gene domain.

To try to explain these results, the Inventors investigated whether mitosis affects the density of the loop attachment sites within the rDNA domain. The chromatin loop sizes were measured using the "Maximum Fluorescent Halo Technique" (Vogelstein et al., 1980). In this method, nuclei were first treated with high salt and then briefly irradiated with UV in the presence of ethidium bromide, which causes extended DNA loops to form a fluorescent halo around the residual nuclear structure (FIG. 4D and Materials and Methods). The loop size was estimated based on the diameter of the fluorescent halo (Buongiorno-Nardelli et al., 1982; Vogelstein et al., 1980), which could be distinguished from the residual nucleoskeleton by immunolocalization of the nuclear lamina (FIG. 4E). FIG. 4F, panel (a), shows that erythrocyte nuclei have a mean loop size of 97.1+/−6.8 kbp, similar to what is seen in other somatic cell nuclei (data not shown and (Buongiorno-Nardelli et al., 1982; Vogelstein et al., 1980)). While this size did not change when nuclei were permeabilized and incubated in S-phase egg extracts (FIG. 4F, b), exposure to an M-phase egg extract prior to calcium activation caused the loop size to decrease to 15.4+/−3.1 kbp (FIG. 4F, c), close to the value of sperm nuclei or early embryonic nuclei in S-phase (FIG. 4F, d, and FIG. 6C).

The Inventors conclude that passage through M-phase prior to S phase induction induces two kinds of rearrangements in erythrocyte nuclei: First, it reduces the loop size, consistent with a higher density of anchorage sites to the nuclear matrix. Second, it decreases the average spacing of replication origins in parallel proportions. In both cases, the organization of chromatin domains becomes similar to that of sperm nuclei entering S phase.

Topoisomerase II is Involved in Replicon Resetting at M Phase.

Since introducing sperm chromatin into mitotic egg extracts causes the chromosomes to condense (Lohka and Masui, 1983), the Inventors next investigated whether chromosome condensation, driven by topoisomerase II in *Xenopus* M-phase egg extracts (Adachi et al., 1991; Wood and Earnshaw, 1990), is involved in replicon resetting in erythrocyte nuclei. While erythrocyte nuclei replicated efficiently when conditioned in the M-phase extract for 45 min prior to S-phase induction (FIG. 1 and FIG. 5A), replication was slow when they were introduced into an M-phase extract and then immediately driven into S phase (FIG. 5A). This showed that it is not the M-S transition that is critical for reorganizing the nuclei for rapid replication, but rather the formation of mitotic metaphase chromosomes. Consistent with this, erythrocyte nuclei that were incubated for 45 min in M-phase extract and then directly transferred to an S-phase extract, but without $Ca^{2+}$ activation, also replicated as efficiently as sperm nuclei (Supplementary FIG. 3).

It has previously been observed that chicken erythrocyte nuclei do not condense in topoisomerase II-depleted extracts (Adachi et al., 1991). Consistent with this, the Inventors found that the topoisomerase II-specific inhibitor ICRF 193 (Oestergaard et al., 2004; Sato et al., 1997) prevented chromosome condensation in erythrocyte or sperm nuclei incubated in an M-phase extract (FIG. 5B). When erythrocyte nuclei were incubated for 45 min in M-Phase extract containing ICRF 193, the Inventors also obtained a very low rate of replication (FIG. 5A). The Inventors confirmed that the ICRF193-containing extract were still in mitosis by measuring H1 kinase activity (Supplementary FIG. 4). The Inventors also obtained similar results when erythrocytes were incubated in topoisomerase II-depleted M-phase extracts (Supplementary FIG. 5). In contrast, topoisomerase II inhibition or depletion did not affect the replication of sperm chromatin in interphase egg extracts, as previously published (Takasuga et al., 1995), although replication did decelerate in the final stages of DNA replication due to decatenation inhibition (Supplementary FIG. 5).

The Chromatin Source, not ORC Protein Levels, Influences Initiation Factor Recruitment The Inventors next addressed the possibility that DNA topoisomerase II dependant chromosomal organisation controls the efficiency of ORC recruitment to chromatin. As shown in FIG. 5C, ORC2 did not bind to erythrocyte or sperm chromatin incubated in M-phase extracts, consistent with previous reports (Romanowski et al., 1996). When S-phase entry was induced by $Ca^{2+}$, ORC2 recruitment onto M-phase extract-treated erythrocyte chromatin was as efficient as it was onto sperm chromatin. ICRF 193 inhibition of topoisomerase II activity during mitotic remodeling, however, dramatically reduced the recruitment of ORC2 onto erythrocyte, but not sperm chromatin for the subsequent S-phase (FIG. 5C). This indicates that the topoisomerase II-dependent mitotic remodeling of erythrocyte nuclei is required for the proper recruitment of ORC proteins in preparation for S phase.

It has been suggested that the absolute amount of replication factors in extracts can explain the observed high rates of DNA replication, and that these factors are titrated by the DNA that accumulates during the rapid divisions. This stoichiometric model was supported by the increased replicon size observed when nuclei concentrations are increased in *Xenopus* egg extracts (Walter and Newport, 1997). The data, however, showed that the concentration of replication proteins could not explain the ability of M-phase extract to program nuclei for rapid DNA replication. One limiting factor could be the ability of nuclei to recruit these proteins. Indeed, FIG. 5D shows that ORC2 is titrated by high concentrations of sperm nuclei, as previously reported (Rowles et al., 1996), but also that the chromatin context dominantly influences the efficiency of this recruitment. With sperm chromatin, the titration curve of ORC in the egg extract reached a plateau at 25 ng of DNA, equivalent to the amount in a midblastula-stage embryo (FIGS. 5D, E). A similar titration curve was observed for MCM3, a subunit of the MCM helicase complex involved in the initiation of DNA replication (data not shown). In contrast, erythrocyte chromatin did not bind ORC2 as efficiently as sperm chromatin (FIGS. 5D, E), and the titration curve had not yet reached a plateau at 50 ng DNA. The recruitment of replication initiation factors is thus not only proportional to the amount of available chromatin, but is also influenced by the chromatin's source.

Rearrangement of Chromatin Domains Occurs with Each Cell Cycle in Early *Xenopus* Development.

In view of the above results, the Inventors investigated whether the same chromatin reorganization occurs during early development in vivo. Early *Xenopus* cell cycles consist of overlapping S and M phases, with no G1 or G2. S phase is initiated at the metaphase-anaphase transition, as individual chromosomes become surrounded by a nuclear membrane to form karyomeres, and before nuclei are reconstructed by the fusion of karyomeres at telophase (FIG. 6A and (Lemaitre et al., 1998; Montag et al., 1988). The Inventors isolated the nuclear matrix either from post-replicative, pre-mitotic nuclei (pre-MBT, 32-64 cell embryos), or from karyomeres subsequent to the metaphase-anaphase transition. Matrix-associated DNA was labeled and used to probe rDNA domain regions (as described above with erythrocyte nuclei; see FIG. 4A). As shown in FIG. 6B, while matrix-associated DNA from post-replicative nuclei was restricted to the rDNA intergenic spacer region, matrix-associated DNA from karyomeres was bound to all rDNA fragments, indicating random association with the matrix. These data provide in vivo confirmation that a major rearrangement of chromatin organization occurs at mitosis, and show that this reorganization occurs with each early embryonic division. The data further suggest that the rapid DNA replication seen during early development involves the use of high numbers of closely-spaced, random attachment points between the chromatin and the nuclear matrix.

According to this interpretation, early mitoses might produce short DNA loop sizes to prepare chromatin for subsequent S phase. The loop size was measured both on karyomeres (S phase entry) or fully reconstituted post-replicative nuclei either from cycloheximide-synchronized early embryos at the 32-64 cell stage (Gard et al., 1990; Lemaitre et al., 1998) and Materials and Methods) or from unsynchronized embryos at the 512-1024 cell stage (Supplementary FIG. 7). FIG. 6C shows that karyomeres had a mean loop size of 17.3+/−7.5 Kbp, similar to that of erythrocyte nuclei following passage through mitosis (FIG. 4F). This loop size also correlates with the replicon size previously measured in vivo during *Xenopus* early development (Hyrien and Mechali, 1993). The loop size increased to 59.7+/−10.7 Kbp in post-replicative early embryonic nuclei (FIG. 6C, and supplementary FIG. 7), confirming the existence of a post-replicative remodeling process that increases the spacing between matrix attachment sites.

If mitotic resetting of chromatin to a short loop size were essential for high initiation rates, then post-replicative nuclei from early embryos that have not passed through mitosis would be incompetent for high rates of DNA replication. Indeed, although obtained from early embryos, post-replicative nuclei that were permeabilized and incubated in an S-phase egg extract replicated slowly relative to sperm nuclei (FIG. 7A), and similarly to erythrocyte nuclei (FIG. 1B). FIG. 7B shows an alkaline agarose gel of nascent DNA that was labeled during DNA replication. With sperm nuclei, strands grew to a value of around 9-10 Kbp, followed by a shift to high molecular weight values, as expected from the joining of replicated DNA from adjacent replicons. With post-replicative nuclei transferred to S phase, such a shift was not observed. DNA replication was less efficient (FIG. 7A), as expected with more widely-spaced replication origins, and a continuous stream of strands growing to larger sizes (>50 Kbp) was observed throughout the reaction. Finally, as previously observed with erythrocyte nuclei (FIGS. 5D, 5E), recruitment of ORC to chromatin was severely diminished, confirming that the efficiency of DNA replication during early development is a matter of chromosome organization and not of the absolute amount of ORC (Supplementary FIG. 8).

The Inventors next addressed whether the increase in loop size was a post-replicative event or occurred during DNA replication. As shown in FIGS. 7C and 7D, loop size increased gradually throughout S phase (FIGS. 7C, D), and this S-phase dependent increase could be prevented with ICRF (data not shown). Finally, the Inventors addressed whether entry into mitosis can reset the large loop size of post-replicative early embryonic nuclei, as previously shown for erythrocyte nuclei. FIG. 7C shows that the loop size in post-replicative embryonic nuclei introduced into M-phase egg extracts was dramatically reduced to 11.2+/−2.6 kbp, a value equivalent to that of sperm chromatin following incubation in mitotic extract or at the beginning of S phase (FIG. 7). This mitotic remodeling of post-replicative nuclei was again blocked by the topoisomerase II inhibitor ICRF193 (FIG. 7C). The Inventors conclude that entry into mitosis resets the loop size of both post-replicative early embryonic nuclei and differentiated nuclei to a low value.

Conclusion

The Dynamic Organization of Nuclear Structures for DNA Replication During Early Development

*Xenopus* early development provides a good illustration of the plasticity of the nuclear structure for adapting to rapid cell cycles (30 min) and DNA replication. Using cellular and biochemical techniques, the Inventors describe here specific features of early nuclear organization, including non-specific anchorage of DNA to the nuclear matrix, short loops, and a close mean spacing between replication origins.

The data, summarized in FIG. 8, indicate that at S phase entry in early development, nuclei are organized into short loops and replicons, allowing recruitment of a large amount of ORC protein. At this stage, DNA replication initiates non-specifically (Hyrien et al., 1995). Loop size increases progressively during S phase, and mitosis reprograms nuclei so that they again include short loops and small replicons, enabling the rapid DNA replication of the early embryo. Topoisomerase II, which has been previously identified as a major component of the chromosomal scaffold or matrix (Berrios et al., 1985; Earnshaw et al., 1985; Gasser et al., 1986), and which is required at an early stage of chromosome condensation, is required for remodeling chromosomal loops and thus for the reprogramming of nuclei for rapid replication.

A probable second, apparently-independent mechanism involves histone acetylation, as inhibition of histone acetylases decreases replication, and this inhibition can be rescued by histone acetylase activators. The steady state endogeneous level of chromatin acetylation in early embryos, however, is sufficient for a maximum rate of sperm DNA replication. The data cannot exclude the additional possibility that DNA replication factors are regulated by acetylation (Takei et al., 2001). In either case, acetylation appears to be required for the accelerated rate of DNA replication observed during early development.

DNA Replication and Chromatin Domain Organization

ORC binding to chromatin has been shown to be linked to origin spacing in *Xenopus* egg extracts (Rowles et al., 1999; Walter and Newport, 1997). As ORC is absent from mitotic chromatin ((Romanowski et al., 1996) and FIG. 5C), the results indicate that mitotic remodeling occurs independently of pre-RC establishment. At the same time, mitotic remodeling, and the associated decrease in loop size, enhances the ability of chromatin to bind ORC. While chromatin-bound ORC increases with the amount of sperm chromatin, at least until the MBT (4,000 to 8,000 cells), the increase is several times lower in post-replicative embryonic nuclei and erythrocyte nuclei. In these nuclei, decreased ORC binding occurs in striking conjunction with an increased DNA loop size, and inhibiting loop size remodeling with ICRF-93 decreases ORC recruitment. A maximum number of ORC-binding sites, corresponding to multiple matrix anchorage sites, might explain the high density of replication initiation sites prior to the MBT. While no strict DNA sequence specificity has been detected for ORC proteins in metazoans or in fission yeast, yeast ORC4 specifically binds to asymmetric AT rich sequences (Chuang and Kelly, 1999), and *Xenopus* ORC preferentially associates with AT rich regions (Kong et al., 2003). AT rich regions are enriched at matrix associated regions (MAR), and this may provide a basal nuclear architecture for DNA replication.

Chromosomal Architecture at Mitosis, Replicon Resetting, and Cloning

A major issue in nuclear transfer experiments is how genetic or epigenetic marks within differentiated nuclei can be erased, as failure to do so decreases cloning efficiency. Cloning success is increased by serial transfer, in which donor nuclei are obtained from embryos that have passed through successive cell divisions following an initial transfer (Gurdon, 1962). The data explain this observation, and suggest that formation of chromosomes at mitosis is an important element in the genetic reprogramming that occurs in successful nuclear transplantation, permitting the restructuring of adult nuclei for rapid embryonic DNA replication.

One model that has been proposed to explain why *Xenopus* nuclear transplants often fail to develop invokes a cytoplasmic clock that imposes cell division every 30 minutes during early development (Hara et al., 1980). In terms of this model, nuclei from differentiated cells that have not been reprogrammed by the time mitosis begins will not be completely replicated, leading to abortive cleavage. Prior exposure to a mitotic egg extract, however, may allow them to keep up with the cell cycle clock by allowing an increased number of replication origins.

The data suggest that it is metaphase, and not the metaphase-anaphase transition, that resets the replicon organization. In classical nuclear transfer, when a somatic donor nuclei is introduced into an egg, the egg is simultaneously activated, triggering an immediate exit from metaphase of the second division and thereby preventing mitotic chromosomes from forming. Significantly, when erythrocyte nuclei are introduced into M phase extracts and immediately driven into S phase, they fail to replicate efficiently. The Inventors found that such nuclei can only be remodeled and efficiently participate in subsequent DNA replication when they are placed in a mitotic environment for 45 min prior to activation (FIG. 1B). Several lines of evidence indicate that the crucial parameter controlling this phenomenon is the organization of metaphase mitotic chromosomes, not the concentration of replication factors. First, the Inventors found that the stoichiometry between replication initiation factors and available chromatin cannot explain the observed rates of ORC recruitment and DNA replication. Second, M phase induces a global change in the chromosomal architecture, leading to a dramatic shortening of chromosome loop size. Third, topoisomerase II, which is involved in regulating chromosomal architecture and has been identified at the base of the loop domains (Adachi et al., 1989; Earnshaw et al., 1985; Gasser et al., 1986; Iarovaia et al., 1995), is necessary for ORC recruitment as well as the shortening of both loop size and inter-origin spacing.

The data may also explain observations showing that the specification of DNA replication origins occurs between the middle and end of G1 phase (Wu and Gilbert, 1996). During early *Xenopus* development, S phase and M phase occur successively without G1. Following the chromatin reprogramming that occurs in mitosis, this lack of G1 may prevent specific origins from being established, resulting in S-phase without specified origins. This required mitotic reprogramming of the replicon and chromosome structure can also explain the observed benefit of the use of half-cleaved embryos as a donor source in animal cloning by serial transfer (Gurdon and Laskey, 1970; Gurdon et al., 1975). Specifically, as such nuclei were presumably exposed to a mitotic context in a first unsuccessful cleavage, they may have been reprogrammed through the mechanism described here. The mechanism also provides an explanation for recent improvements in human cloning methods in which a two-hour incubation between nuclear injection and egg activation increases the cloning efficiency (Hwang et al., 2005).

Because the sperm and egg nuclei replicate before karyogamy, the Inventors expect that they must be organized for rapid DNA replication by the time they fuse, before the first mitotic division. Indeed, before fertilization occurs the egg nucleus is blocked at metaphase and is therefore already organized into mitotic chromosomes. In addition, the Inventors observed that sperm nuclei were organized into short loops before fertilization, indicating that both the male and female pronuclei are already set for rapid replication at fertilization. These observations underscore the fact that it is unfertilized eggs, but not activated or fertilized eggs, that are capable of conditioning differentiated nuclei for development.

Example 2

Method for Increasing Cloning Efficiency

Material and Methods

*Xenopus* egg mitotic extracts are used to form mitotic chromosomes from a nucleus of a differentiated somatic cell, in order to improve the efficiency of the cloning by nuclear transfer.

The nuclei are purified as follows: the cells are collected and centrifuged at 1000 g for 10 minutes. The cells are washed with PBS before being centrifuged at 1000 g for 10 minutes. Then, the cells are resuspended in 10 ml of a cold hypotonic buffer (4° C.) (HB: 10 mM K/Hepes pH 7.7, 10 mM KCl, 1 mM NaCl, 2 mM $MgCl_2$, 1 mM EGTA), before being transferred in a dounce homogenizer tight pestle B for 10 minutes, until the cells are swelled. Then, the dounce strokes are carried out until the cellular membrane has disappeared (10 to 15 dounce strokes, depending on the cell type). The mixture is then centrifuged at 1000 g for 10 minutes. The pellet is resuspended in a hypotonic buffer 0.1% Triton X100. The nuclei are purified through a sucrose cushion of sucrose 0.7 M and resuspended in a remodeling buffer RB (10 mM Hepes/K pH 7.3, 100 mM KCl, 0.1 mM $CaCl_2$, 1 mM $MgCl_2$, 50 mM sucrose).

The mitotic remodeling is carried out by mixing 22 µl of *Xenopus* egg mitotic extract with 2.5 µl of E mix (200 µg/ml creatine kinase, 200 mM creatine phosphate, 20 mM ATP, 20 mM $MgCl_2$ 2 mM EGTA) and 0.5 µl of differentiated and purified nuclei (500 nuclei/µl of extract). The mixture is incubated for 45 minutes (up to 1 hour 30 minutes) at 23° C. in order to form chromosomes.

When cloning is performed from cells, and not from the purified nuclei, the cells are first possibly permeabilized as follows: cultured cells are washed with PBS and are resuspended in a permeabilization buffer (CPB: 10 mM K/Hepes pH 7.7, 100 mM KCl, 5 mM NaCl, 2 mM $MgCl_2$, 1 mM EGTA protease inhibitors, Leupeptin, Pepstatin, Aprotinin at 10 µg/ml) cooled down on ice adjusted at $10.10^6$/ml. Digitonin at a final concentration of 30 µg/ml is added for 5 min at 4° C. The reaction is then stopped by adding 10 volumes of PB, protease inhibitors. The mixture is centrifuged at 1000 g for 10 minutes, and the cells are resuspended at $10^8$ cells/ml of PB, 10% glycerol, protease inhibitors. Freshly prepared cells are used. The mitotic remodeling is then carried out as previously, at a concentration of around 500 cells/μl of extract.

Cells or nuclei are then injected in an enucleated ovule to trigger the development. This protocol may be used for cells of different animal species.

Results

Animal cloning is now possible but used with low yields of success that differ between species. The Inventors have demonstrated the ability of a *Xenopus* egg extract to reprogram a nucleus of a differentiated somatic cell. During early embryogenesis of *Xenopus*, the S-phase length is reduced to 15 minutes, whereas the S-phase generally lasts 6-8 hours in a somatic cell. This replication rate is particularly high because of an increase in the number of replication origins which function on the genome upon each cycle in an almost synchronous way.

The results of the Inventors show that the reprogramming of a differentiated nucleus can only occur during the incubation with a mitotic extract, which leads to the formation of metaphase chromosomes. The Inventors have then measured the ability of the reprogrammed nucleus to reproduce a replication phase which is characteristic of the early development, with a number of replication origins corresponding to an embryo of this stage. This reprogramming occurs through a complete genome reorganization to adapt the genome to short cycles (Lemaitre et al., 2005, 123(5):787-801)). The Inventors have also demonstrated that this phenomenon of genome adaptation is a main phenomenon of the embryo which operates upon each cycle, which ensures a complete duplication of the genome before mitosis, otherwise leading to a genomic instability.

Example 3

Method for Obtaining Stem Cells from a Differentiated Somatic Cell

The following process may be used for obtaining stem cells from any kind of differentiated somatic cell.

The cells, for example blood cells, are purified and permeabilized as follows: the cultured cells are washed in 10 ml PBS, then centrifuged at 1000 g for 10 min. The cell pellet is resuspended in 10 ml of permeabilization buffer PB (10 mM K/Hepes pH 7.7, 100 mM KCl, 5 mM NaCl, 2 mM $MgCl_2$, 1 mM EGTA). The cells are centrifuged at 1000 g for 10 min and the cell pellet is resuspended in PB, protease inhibitors (mix of Leupeptin, Pepstatin, Aprotinin, each at 10 μg/ml). The cells are then put on ice and adjusted to a concentration of $10.10^6$ cells/ml.

The cells are permeabilized by adding digitonin (30 mg/ml of a stock solution) at a final concentration of 30 μg/ml, for 5 min on ice (4° C.). The reaction is stopped by adding 10 volumes of PB, protease inhibitors. The cells are then centrifuged at 1000 g for 10 min.

In a typical remodeling reaction, 22 μl of M phase extract are mixed with 0.5 μl of permeabilized cells or nuclei (500 nuclei or cells/μl extract). The mixture is incubated at 23° C. for 45 min. The cells are then washed in PBS to remove the cell extract and are seeded in a culture plate.

REFERENCES

Adachi, Y., Kas, E., and Laemmli, U. K. (1989). Preferential, cooperative binding of DNA topoisomerase II to scaffold-associated regions. Embo J 8, 3997-4006.

Adachi, Y., and Laemmli, U. K. (1992). Identification of nuclear pre-replication centers poised for DNA synthesis in *Xenopus* egg extracts: immunolocalization study of replication protein A. J Cell Biol 119, 1-15.

Adachi, Y., Luke, M., and Laemmli, U. K. (1991). Chromosome assembly in vitro: topoisomerase II is required for condensation. Cell 64, 137-148.

Aggarwal, B. D., and Calvi, B. R. (2004). Chromatin regulates origin activity in *Drosophila* follicle cells. Nature 430, 372-376.

Almouzni, G., and Mechali, M. (1988). Assembly of spaced chromatin promoted by DNA synthesis in extracts from *Xenopus* eggs. Embo J 7, 665-672.

Balasubramanyam, K., Swaminathan, V., Ranganathan, A., and Kundu, T. K. (2003). Small molecule modulators of histone acetyltransferase p 300. J Biol Chem 278, 19134-19140.

Berezney, R., Dubey, D. D., and Huberman, J. A. (2000). Heterogeneity of eukaryotic replicons, replicon clusters, and replication foci. Chromosoma 108, 471-484.

Berezney, R., Mortillaro, M. J., Ma, H., Wei, X., and Samarabandu, J. (1995). The nuclear matrix: a structural milieu for genomic function. Int Rev Cytol, 1-65.

Berrios, M., Osheroff, N., and Fisher, P. A. (1985). In situ localization of DNA topoisomerase II, a major polypeptide component of the Drosophila nuclear matrix fraction. Proc Natl Acad Sci Usa 82, 4142-4146.

Blow, J. J., and Laskey, R. A. (1986). Initiation of DNA replication in nuclei and purified DNA by a cell-free extract of *Xenopus* eggs. Cell 47, 577-587.

Buongiorno-Nardelli, M., Micheli, G., Carri, M. T., and Marilley, M. (1982). A relationship between replicon size and supercoiled loop domains in the eukaryotic genome. Nature 298, 100-102.

Chuang, R. Y., and Kelly, T. J. (1999). The fission yeast homologue of Orc4p binds to replication origin DNA via multiple AT-hooks. Proc Natl Acad Sci USA 96, 2656-2661.

Cook, P. R., and Brazell, I. A. (1975). Supercoils in human DNA. J Cell Sci 19, 261-286.

Cook, P. R., and Brazell, I. A. (1976). Conformational constraints in nuclear DNA. J Cell Sci 22.

Coue, M., Kearsey, S. E., and Mechali, M. (1996). Chromotin binding, nuclear localization and phosphorylation of *Xenopus* cdc21 are cell-cycle dependent and associated with the control of initiation of DNA replication. Embo J 15, 1085-1097.

Danis, E., Brodolin, K., Menut, S., Maiorano, D., Girard-Reydet, C., and Mechali, M. (2004). Specification of a DNA replication origin by a transcription complex. Nat Cell Biol 6, 721-730.

DiBerardino, M. A., and Hoffner, N. J. (1983). Gene reactivation in erythrocytes: nuclear transplantation in oocytes and eggs of Rana. Science 219, 862-864.

Dijkwel, P. A., Vaughn, J. P., and Hamlin, J. L. (1991). Mapping of replication initiation sites in mammalian genomes by two-dimensional gel analysis: stabilization and enrichment of replication intermediates by isolation on the nuclear matrix. Mol Cell Biol 11, 3850-3859.

Earnshaw, W. C., Halligan, B., Cooke, C. A., Heck, M. M., and Liu, L. F. (1985). Topoisomerase II is a structural component of mitotic chromosome scaffolds. J Cell Biol 100, 1706-1715.

Firmbach-Kraft, I., and Stick, R. (1995). Analysis of nuclear lamin isoprenylation in *Xenopus* oocytes: isoprenylation of lamin B3 precedes its uptake into the nucleus. J Cell Biol 129, 17-24.

Francon, P., Lemaitre, J. M., Dreyer, C., Maiorano, D., Cuvier, O., and Mechali, M. (2004). A hypophosphorylated form of RPA34 is a specific component of pre-replication centers. J Cell Sci 117, 4909-4920.

Gard, D. L., Hafezi, S., Zhang, T., and Doxsey, S. J. (1990). Centrosome duplication continues in cycloheximide-treated Xenopus blastulae in the absence of a detectable cell cycle. J Cell Biol 110, 2033-2042.

Gasser, S. M., and Laemmli, U. K. (1986). Cohabitation of scaffold binding regions with upstream/enhancer elements of three developmentally regulated genes of D. melanogaster. Cell 46, 521-530.

Gasser, S. M., Laroche, T., Falquet, J., Boy de la Tour, E., and Laemmli, U. K. (1986). Metaphase chromosome structure. Involvement of topoisomerase II. J Mol Biol 188, 613-629.

Gurdon, J. B. (1962). The developmental capacity of nuclei taken from intestinal epithelium cells of feeding tadpoles. J Embryol Exp Morphol 10, 622-640.

Gurdon, J. B., Byrne, J. A., and Simonsson, S. (2003). Nuclear reprogramming and stem cell creation. Proc Natl Acad Sci USA 100 Suppl 1, 11819-11822.

Gurdon, J. B., and Laskey, R. A. (1970). The transplantation of nuclei from single cultured cells into enucleate frogs' eggs. J Embryol Exp Morphol 24, 227-248.

Gurdon, J. B., Laskey, R. A., and Reeves, O. R. (1975). The developmental capacity of nuclei transplanted from keratinized skin cells of adult frogs. J Embryol Exp Morphol 34, 93-112.

Hara, K., Tydeman, P., and Kirschner, M. (1980). A cytoplasmic clock with the same period as the division cycle in Xenopus eggs. Proc Natl Acad Sci USA 77, 462-466.

Hozak, P., Hassan, A. B., Jakson, D. A., and Cook, P. R. (1993). Visualization of replication factories attached to a nucleoskeleton. Cell 73, 361-373.

Hwang, W. S., Roh, S. I., Lee, B. C., Kang, S. K., Kwon, D. K., Kim, S., Kim, S. J., Park, S. W., Kwon, H. S., Lee, C. K., et al. (2005). Patient-specific embryonic stem cells derived from human SCNT blastocysts. Science 308, 1777-1783.

Hyrien, O., Maric, C., and Mechali, M. (1995). Transition in specification of embryonic metazoan DNA replication origins. Science 270, 994-997.

Hyrien, O., and Mechali, M. (1993). Chromosomal replication initiates and terminates at random sequences but at regular intervals in the ribosomal DNA of Xenopus early embryos. Embo J 12, 4511-4520.

Iarovaia, O. V., Lagarkova, M. A., and Razin, S. V. (1995). The specificity of human lymphocyte nucleolar DNA long-range fragmentation by endogenous topoisomerase II and exogenous Bal 31 nuclease depends on cell proliferation status. Biochemistry 34, 4133-4138.

Ioudinkova, E., Petrov, A., Razin, S. V., and Vassetzky, Y. S. (2005). Mapping long-range chromatin organization within the chicken alpha-globin gene domain using oligonucleotide DNA arrays. Genomics 85, 143-151.

Jackson, D. A. (1990). The organization of replication centres in higher eukaryotes. Bioessays 12, 87-89.

Kong, D., Coleman, T. R., and DePamphilis, M. L. (2003). Xenopus origin recognition complex (ORC) initiates DNA replication preferentially at sequences targeted by Schizosaccharomyces pombe ORC. Embo J 22, 3441-3450.

Lemaitre, J. M., Bocquet, S., Buckle, R., and Mechali, M. (1995). Selective and rapid nuclear translocation of a c-Myc-containing complex after fertilization of Xenopus laevis eggs. Mol Cell Biol 15, 5054-5062.

Lemaitre, J. M., Bocquet, S., and Mechali, M. (2002). Competence to replicate in the unfertilized egg is conferred by Cdc6 during meiotic maturation. Nature 419, 718-722.

Lemaitre, J. M., Geraud, G., and Mechali, M. (1998). Dynamics of the genome during early Xenopus laevis development: karyomeres as independent units of replication. J Cell Biol 142, 1159-1166.

Leno, G. H., and Laskey, R. A. (1991). The nuclear membrane determines the timing of DNA replication in Xenopus egg extracts. J Cell Biol 112, 557-566.

Leonard, R. A., Hoffner, N. J., and DiBerardino, M. A. (1982). Induction of DNA synthesis in amphibian erythroid nuclei in Rana eggs following conditioning in meiotic oocytes. Dev Biol 92, 343-355.

Lohka, M. J., and Masui, Y. (1983). Formation in vitro of sperm pronuclei and mitotic chromosomes induced by amphibian ooplasmic components. Science 220, 719-721.

Lu, Z. H., Xu, H., and Leno, G. H. (1999). DNA replication in quiescent cell nuclei: regulation by the nuclear envelope and chromatin structure. Mol Biol Cell 10, 4091-4106.

McKay, R. (2000). Stem cells-hype and hope. Nature 406, 361-364.

Menut, S., Lemaitre, J. M., Hair, A., and Méchali, M. (1999). DNA replication and chromatin assembly using Xenopus egg extracts., Oxford University Press, Ed J. D. Richter.).

Michalet, X., Ekong, R., Fougerousse, F., Rousseaux, S., Schurra, C., Hornigold, N., van Slegtenhorst, M., Wolfe, J., Povey, S., Beckmann, J. S., and Bensimon, A. (1997). Dynamic molecular combing: stretching the whole human genome for high-resolution studies. Science 277, 1518-1523.

Montag, M., Spring, H., and Trendelenburg, M. F. (1988). Structural analysis of the mitotic cycle in pre-gastrula Xenopus embryos. Chromosoma 96, 187-196.

Murray, A. W. (1991). Cell cycle extracts. Methods Cell Biol 36, 581-605.

Nakayasu, H., and Berezney, R. (1989). Mapping replicational sites in the eucaryotic cell nucleus. J Cell Biol 108, 1-11.

Neri, L. M., Mazzotti, G., Capitani, S., Maraldi, N. M., Cinti, C., Baldini, N., Rana, R., and Martelli, A. M. (1992). Nuclear matrix-bound replicational sites detected in situ by 5-bromodeoxyuridine. Histochemistry 98, 19-32.

Oestergaard, V. H., Knudsen, B. R., and Andersen, A. H. (2004). Dissecting the cell-killing mechanism of the topoisomerase II-targeting drug ICRF-193. J Biol Chem 279, 28100-28105.

Pardoll, D. M., and Vogelstein, B. (1980). Sequence analysis of nuclear matrix associated DNA from rat liver. Exp Cell Res 128, 466-470.

Pasero, P., Bensimon, A., and Schwob, E. (2002). Single-molecule analysis reveals clustering and epigenetic regulation of replication origins at the yeast rDNA locus. Genes Dev 16, 2479-2484.

Paulson, J. R., and Laemmli, U. K. (1977). The structure of histone-depleted metaphase chromosomes. Cell 12, 817-828.

Romanowski, P., Madine, M. A., Rowles, A., Blow, J. J., and Laskey, R. A. (1996). The Xenopus origin recognition complex is essential for DNA replication and MCM binding to chromatin. Curr Biol 6, 1416-1425.

Rowles, A., Chong, J. P., Brown, L., Howell, M., Evan, G. I., and Blow, J. J. (1996). Interaction between the origin recognition complex and the replication licensing system in Xenopus. Cell 87, 287-296.

Rowles, A., Tada, S., and Blow, J. J. (1999). Changes in association of the *Xenopus* origin recognition complex with chromatin on licensing of replication origins. J Cell Sci 112, 2011-2018.

Ryan, J., Llinas, A. J., White, D. A., Turner, B. M., and Sommerville, J. (1999). Maternal histone deacetylase is accumulated in the nuclei of *Xenopus* oocytes as protein complexes with potential enzyme activity. J Cell Sci 112 (Pt 14), 2441-2452.

Sato, M., Ishida, R., Ohsumi, K., Narita, T., and Andoh, T. (1997). DNA topoisomerase II as the cellular target of a novel antitumor agent ICRF-193, a bisdioxopiperazine derivative, in *Xenopus* egg extract. Biochem Biophys Res Commun 235, 571-575.

Takasuga, Y., Andoh, T., Yamashita, J., and Yagura, T. (1995). ICRF-193, an inhibitor of topoisomerase II, demonstrates that DNA replication in sperm nuclei reconstituted in *Xenopus* egg extracts does not require chromatin decondensation. Exp Cell Res 217, 378-384.

Takei, Y., Swietlik, M., Tanoue, A., Tsujimoto, G., Kouzarides, T., and Laskey, R. (2001). MCM3AP, a novel acetyltransferase that acetylates replication protein MCM3. EMBO Rep 2, 119-123.

Tunquist, B. J., and Maller, J. L. (2003). Under arrest: cytostatic factor (CSF)-mediated metaphase arrest in vertebrate eggs. Genes Dev 17, 683-710.

Vassetzky, Y., Hair, A., and Mechali, M. (2000). Rearrangement of chromatin domains during development in *Xenopus*. Genes Dev 14, 1541-1552.

Versini, G., Comet, I., Wu, M., Hoopes, L., Schwob, E., and Pasero, P. (2003). The yeast Sgs1 helicase is differentially required for genomic and ribosomal DNA replication. Embo J 22, 1939-1949.

Vogelstein, B., Pardoll, D. M., and Coffey, D. S. (1980). Supercoiled loops and eucaryotic DNA replicaton. Cell 22, 79-85.

Wade, P. A., Jones, P. L., Vermaak, D., and Wolffe, A. P. (1999). Purification of a histone deacetylase complex from *Xenopus laevis*: preparation of substrates and assay procedures. Methods Enzymol 304, 715-725.

Walter, J., and Newport, J. (2000). Initiation of eukaryotic DNA replication: origin unwinding and sequential chromatin association of Cdc45, RPA, and DNA polymerase alpha. Mol Cell 5, 617-627.

Walter, J., and Newport, J. W. (1997). Regulation of replicon size in *Xenopus* egg extracts. Science 275, 993-995.

Wood, E. R., and Earnshaw, W. C. (1990). Mitotic chromatin condensation in vitro using somatic cell extracts and nuclei with variable levels of endogenous topoisomerase II. J Cell Biol 111, 2839-2850.

Wu, J. R., and Gilbert, D. M. (1996). A distinct G1 step required to specify the Chinese hamster DHFR replication origin. Science 271, 1270-1272.

Wu, J. R., Yu, G., and Gilbert, D. M. (1997). Origin-specific initiation of mammalian nuclear DNA replication in a *Xenopus* cell-free system. Methods 13, 313-324.

The invention claimed is:

1. A method for a mitotic remodeling of chromosomes of differentiated somatic donor cells of pluricellular organisms selected from the group consisting of *Xenopus*, mouse and humans, comprising the step of:
contacting an unactivated female germinal cell (egg) extract of *Xenopus* in M-phase of the cell cycle, said extract containing an amount of EGTA sufficient to chelate $Ca^{2+}$ activity, with one of:
(i) nuclei of the differentiated somatic donor cells of the pluricellular organisms, and
(ii) the differentiated somatic donor cells containing nuclei of the pluricellular organisms,
wherein chromosomes of the resulting contacted donor cells exhibit characteristics of mitotic remodeling.

2. A process for preparing nuclei of differentiated erythrocytes, comprising: contacting *Xenopus* erythrocyte nuclei with an unactivated female germinal cell (egg) extract of *Xenopus* in M-phase of the cell cycle, said extract containing EGTA an amount of EGTA sufficient to chelate Ca2+ activity, wherein said contacting results in decreasing loop size and distance between replication origins.

3. The method according to claim 1, further comprising the step of:
partially or totally removing said unactivated female germinal cell (egg) extract.

* * * * *

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
ggagaggtag agacaagaca gaggc                                             25

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 2
gggcgaagaa aaccgggaga aatac                                             25

<210> SEQ ID NO 3
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 3
gagagaaaga cggaaagaaa ggagagtac                                         29

<210> SEQ ID NO 4
<211> LENGTH: 26
<212> TYPE: DNA
```

```
<213> ORGANISM: Artificial Sequence
<220> FEATURE:
<223> OTHER INFORMATION: Synthetic Oligonucleotide

<400> SEQUENCE: 4
cattcgtatt gtgccagcta gaggtg                                      26

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 5
ccacgactca gacctcagat cagac                                       25

<210> SEQ ID NO 6
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 6
gtaacaactc acctgccgaa tcaacta                                     27

<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 7
ctgtgaagag acatgagagg tgtaggataa                                  30
```